(12) United States Patent
Annis et al.

(10) Patent No.: US 7,145,035 B2
(45) Date of Patent: Dec. 5, 2006

(54) METHODS OF ORTHO ALKYLATION

(75) Inventors: Gary David Annis, Landenberg, PA (US); Richard James Brown, Newark, DE (US); Albert Loren Casalnuovo, Wilmington, DE (US); Stephen Ernest Jacobson, Princeton, NJ (US); Philip Osborne Moss, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 49 days.

(21) Appl. No.: 10/468,637

(22) PCT Filed: Mar. 14, 2002

(86) PCT No.: PCT/US02/07880

§ 371 (c)(1),
(2), (4) Date: Aug. 20, 2003

(87) PCT Pub. No.: WO02/072540

PCT Pub. Date: Sep. 19, 2002

(65) Prior Publication Data

US 2004/0082793 A1   Apr. 29, 2004

Related U.S. Application Data

(60) Provisional application No. 60/275,566, filed on Mar. 14, 2001.

(51) Int. Cl.
C07C 313/00   (2006.01)
C07D 211/72   (2006.01)
(52) U.S. Cl. ...................................... 564/102; 546/312
(58) Field of Classification Search ................ 564/102; 546/312
See application file for complete search history.

(56) References Cited

U.S. PATENT DOCUMENTS

| 3,527,810 A | 9/1970 | Pettitt |
| 4,006,183 A | 2/1977 | Jackson |
| 4,404,069 A | 9/1983 | Goodin et al. |
| 4,496,765 A | 1/1985 | Ku et al. |
| 4,806,687 A | 2/1989 | Balthazor et al. |
| 5,449,655 A | 9/1995 | Albers et al. |
| 5,728,887 A | 3/1998 | Jacobson |
| 6,008,384 A | 12/1999 | Bockrath et al. |

FOREIGN PATENT DOCUMENTS

| CA | 1242219 | 9/1988 |
| WO | WO 01/70671 | 9/2001 |

OTHER PUBLICATIONS

Varkey et al, J.O.C. 39,(23), (1974) pp. 3365-3372.*
Gassman et al, Organic Synthesis, vol. 6, p. 581 (1988).*

R. Mozingo, "Palladium Catalysts", Org. Syn., coll. vol. 3, Wiley, New York, 1955, 685-690.
P. Claus et al., "Methylthiomethylierung von Aromatischen Aminen . . . ", Tetrahedron Lett. 1968, 3607-3610.
P. Claus et al., "Methylthiomethylierung von Anilinen und Phenolen . . . ", Monatsch. Chem. 1970, 101, 396-404.
P. Claus et al., "Zum Mechanismus der Umlagerung von . . . ", Monatsch. Chem. 1972, 103, 1163-1177.
P. G. Gassman et al., "Specific Ortho Alkylation of Aromatic Amines", J. Am. Chem. Soc. 1973, 95, 588-589.
T. E. Varkey et al., "Activation of Dimethyl Sulfoxide by Electrophiles . . . ", J. Org. Chem. 1974, 39, 3365-3372.
A.D. Dawson et al. "Iminosulfonium Salts and Iminosulfuranes from", J. Org. Chem., 1977, 42, 592-597.
M. Masai et al., "Dehydrogenation and Hydrogenation Activity . . . ", Journal of Catalysis 1977, 50, 419-428.
P. G. Gassman et al., "The Ortho Functionalization of Aromatic . . . ", J. Am. Chem. Soc., 1978, 100, 7600-7610.
P. G. Gassman et al., "Exclusive Ortho Substitution of Phenols . . . ", J. Am. Chem. Soc., 1978, 100, 7611-7619.

(Continued)

Primary Examiner—Amelia A. Owens

(57) ABSTRACT

The present invention pertains to methods for preparing a compound of Formula (I), wherein A is O or N-L; each L is independently H or an acyl group; K is, together with the two contiguous linking carbon atoms, a phenyl ring, a 5- or 6-membered heteroaromatic ring or an aromatic 8-, 9- or 10-membered fused carbobicyclic or heterobicyclic ring system wherein each ring or ring system is optionally substituted; $R^1$ is H, $C_1$ to $C_4$ alkyl or $CO_2R^3$; $R^2$ is H or $C_1$ to $C_4$ alkyl; and $R^3$ is $C_1$ to $C_4$ alkyl; comprising hydrogenating a compound of Formula (II), wherein n is 0, 1 or 2 in the presence of a catalyst comprising palladium to form the compound of Formula (I). This invention further pertains to methods for preparing compounds of Formula (II) useful for preparing compounds of Formula (I). This invention also pertains to compounds used in these methods

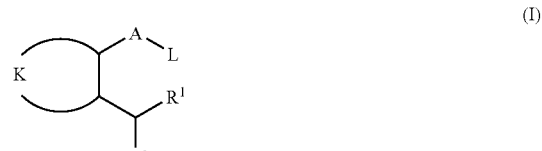

(I)

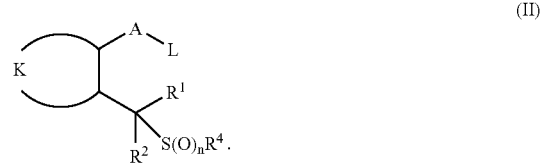

(II)

9 Claims, No Drawings

OTHER PUBLICATIONS

C. Henriques et al., "Influence of Tin of the Stability of Sn/Pd...", Applied Catalysis 1986, 21, 169-177.

P. G. Gassman et al., "ortho-Alkylation of Anilines...", Org. Syn., Coll. vol. 6, Wiley, New York, 1988, 581-583.

H. R. Aduriz et al., "Alumina-Supported Bimetallics of Palladium Alloyed...", J. of Catalysis 1989, 199, 97-107.

V. L. Mylroie et al., "Reduction of Sulfonyl Chlorides to Thiols...", Catalysis of Organic Reactions, D.W. Blackburn, Ed., Marcel Dekker Inc., New York, 1990, pp. 189-196.

P. Claus et al., "Effect of Zn and Sn on the Chemoselectivity and...", Chem. Ing. Tech. 1993, 65(5), 569-572.

* cited by examiner

US 7,145,035 B2

METHODS OF ORTHO ALKYLATION

REFERENCE TO RELATED APPLICATIONS

This application is a national filing under 35 U.S.C. 371 of International Application No. PCT/US02/07880, filed 14 Mar. 2002, which claims priority benefit of Provisional Application 60/275,566, filed 14 Mar. 2001.

FIELD OF THE INVENTION

The present invention pertains to improved methods for the preparation of ortho alkylated aromatic alcohols and amines.

BACKGROUND OF THE INVENTION

Orthoalkylated anilines and phenols are important building blocks in the preparation of plant protection agents, pharmaceuticals and other fine chemicals. Classical Friedel-Crafts alkylation of anilines and phenols typically leads to para as well as ortho alkylation, and furthermore often results in polyalkylation. While Friedel-Crafts acylation of anilines and phenols typically gives only monosubstitution, substitution still can occur at the para as well as ortho positions, and reaction conditions needed for reductive removal of the acyl carbonyl moiety may be incompatible with other functionality on the molecule.

In the 1970s, Paul Gassman led the development of an alternative synthetic method affording regioselective orthoalkylation (for lead references see P. G. Gassman and G. Gruetzmacher, *J. Am. Chem. Soc.* 1973, 95, 588–589; P. G. Gassman and G. Gruetzmacher, *Org. Syn.*, Coll. Vol. VI, 581–583; P. G. Gassman and H. R. Drewes, *J. Am. Chem. Soc.* 1978, 100, 7600–7610; P. G. Gassman and D. R. Amick, *J. Am. Chem. Soc.* 1978, 100, 7611–7619). The Gassman method involves generating an intermediate species believed to have the Formula i from the aniline or phenol and an alkyl thioether such as dimethyl sulfide and oxidizing agents such as tert-butyl hypochlorite or chlorine.

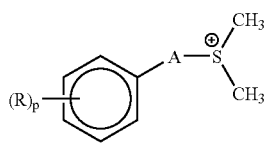

i wherein A is NH or O, and $(R)_p$ denotes optional substituents.

Treatment with base such as triethylamine or sodium methoxide effects rearrangement to give an ortho alkylthioalkyl compound illustrated by Formula ii.

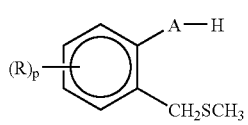

ii wherein A is NH or O, and $(R)_p$ denotes optional substituents.

Lastly, desulfurization treatment with Raney nickel cleaves the alkylthioalkyl group to an alkyl group as illustrated by Formula iii.

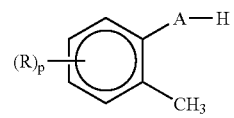

iii wherein A is NH or O, and $(R)_p$ denotes optional substituents.

While this method offers an attractive alternative to Friedel-Crafts methods of aromatic alkylation, its conditions are not ideal for preparation on an industrial scale. Particularly disadvantageous is its use of Raney nickel to cleave the alkylthioalkyl group to alkyl. Raney nickel is used as a reagent instead of a true catalyst and thus is expensive. Moreover, it is pyrophoric and must be kept covered with water. Although slurrying the spent material in water and flushing down the drain is suggested by P. G. Gassman, G. Gruetzmacher, *Org. Syn.*, Coll. Vol. VI, 581–583, this article recognizes such disposal to be environmentally unsound. A more satisfactory alternative to Raney nickel is needed for industrial manufacture using this method.

Another disadvantage of this method is that the procedures used to prepare species illustrated by Formula i often rely upon cold temperatures, as low as −50° C. As refrigeration is expensive, the need to maintain such low temperatures is undesirable in industrial manufacture of chemicals.

A. D. Dawson and D. Swern (*J. Org. Chem.* 1977, 42, 592–597) report preparation and isolation of the species illustrated by Formula i by treatment of anilines with dimethyl sulfide activated by N-chlorosuccinimide or N-chlorobenzotriazole, again at low temperatures. This reference does not disclose rearrangement to compounds illustrated by Formula ii. U.S. Pat. No. 4,496,765 discloses preparation of an ylid of Formula iv by washing with aqueous sodium hydroxide solution a dichloromethane solution of the corresponding compound of Formula i, which is formed from 2-(trifluoromethyl)-aniline, dimethyl sulfide and N-chlorosuccinimide.

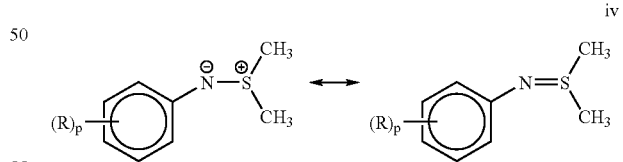

iv wherein $(R)_p$ denotes optional substituents.

U.S. Pat. No. 4,496,765 also discloses preparation of a compound of Formula ii by heating the ylid of Formula iv, optionally in the presence of catalytic succinimide.

P. Claus and W. Vycudilik (*Tetrahedron Lett.* 1968, 3607–3610; *Monatsch. Chem.* 1970, 101, 396–404) report that anilines can be transformed into readily isolable ylids illustrated by Formula iv by treatment with dimethyl sulfoxide, phosphorus pentoxide and triethylamine in chloroform at temperatures near room temperature. In this reaction, the triethylamine base may be presumed to deprotonate an intermediate species illustrated by Formula i. The intermediate ylids illustrated by Formula iv are then reported to rearrange to ortho alkylthioalkyl compounds illustrated by Formula ii in the presence of bases such as triethylamine or in protic solvents such as alcohols and water even without the addition of base (see also P. Claus and W. Rieder, *Monatsh. Chem.* 1972, 103, 1163–1177). As this method avoids need for low temperatures, it is industrially more attractive, but the cost of phosphorus pentoxide and disposing of phosphorus wastes would be of concern industrially. These references do not address the desulfurization conversion of Formula ii to Formula iii.

Because of potentially lower cost and easier treatment of waste, sulfur trioxide is more industrially attractive than phosphorus pentoxide. U.S. Pat. No. 3,527,810 discloses a process for preparing the sulfur trioxide complex with dimethyl sulfoxide, and T. E. Varkey, G. F. Whitfield and D. Swern (*J. Org. Chem.* 1974, 39, 3365–3372) report the use of sulfur trioxide to activate dimethyl sulfoxide in reaction with aromatic amines to form ylids illustrated by Formula iv after treatment with base. For the reaction of the sulfur trioxide complex of dimethyl sulfoxide with p-toluenesulfonamide, this reference reports cosolvents such as chloroform giving lower yields. For the reaction of the sulfur trioxide complex of dimethyl sulfoxide with aromatic amines, this reference avoids a cosolvent and teaches a ratio of $DMSO:SO_3$: aromatic amine of 4–6:1:0.6–0.9, and recommends this over a $DMSO:SO_3$ ratio of 2–3:1. This reference also describes use of acetic anhydride, trifluoroacetic anhydride, trifluoromethanesulfonic anhydride, cyclohexylcarbodiimide and phosphorus pentoxide as activating agents for dimethyl sulfoxide. The reference does not report rearrangement of the ylids from aromatic amines.

None of the above references disclose useful alternatives to Raney nickel for the desulfurization conversion of Formula ii to Formula iii required by this method. U.S. Pat. Nos. 4,404,069 and 4,806,687 disclose such alternatives.

U.S. Pat. No. 4,404,069 uses electrolytic desulfurization to reduce 2-(methylthio-methyl)-6-(trifluoromethyl)aniline or its corresponding sulfoxide or sulfone to 2-methyl-6-(trifluoromethyl)aniline. This method requires use of large amounts of quaternary ammonium salt electrolytes in addition to polar solvents, in which organic substances may not be highly soluble. U.S. Pat. No. 4,404,069 reports that sulfoxides and sulfones are more easily reduced than sulfides. Oxidation of sulfides to sulfoxides or sulfones requires an additional step. An undesirable potential side reaction is reduction of halogen substituents. To avoid reduction of trifluoromethyl to difluoromethyl, U.S. Pat. No. 4,404,069 recommends stopping the reaction before conversions exceed 85–90% or continuously extracting the product from the polar reaction mixture, which may also be needed to prevent phase separation of the reactant and product from the polar reaction medium.

U.S. Pat. No. 4,806,687 uses hydrodesulfurization with a presulfided cobalt-molybdenum catalyst to reduce 2-(methylthiomethyl)-6-(trifluoromethyl)aniline to 2-methyl-6-(trifluoromethyl)aniline. The preferred temperature for this reaction is 150 to 250° C. Moreover, a hydrogen pressure of more than 3400 kPa is preferred to obtain practical reaction rates.

In view of the process requirements and limitations of these methods, further improvements are still needed to effect the desulfurization conversion of Formula ii to Formula iii. Such an improvement has now been discovered.

SUMMARY OF THE INVENTION

The present invention pertains to a method for preparing a compound of Formula I

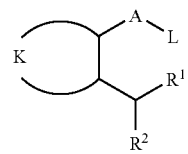

I wherein
A is O or N-L;
each L is independently H or an acyl group;
K is, together with the two contiguous linking carbon atoms, a phenyl ring, a 5- or 6-membered heteroaromatic ring or an aromatic 8-, 9- or 10-membered fused carbobicyclic or heterobicyclic ring system wherein each ring or ring system is optionally substituted;
$R^1$ is H, $C_1$ to $C_4$ alkyl or $CO_2R^3$;
$R^2$ is H or $C_1$ to $C_4$ alkyl; and
$R^3$ is $C_1$ to $C_4$ alkyl;

comprising hydrogenating a compound of Formula II

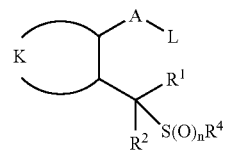

II wherein n is 0, 1 or 2; $R^4$ is $CHR^1R^2$; and A, K, L, $R^1$, $R^2$ and $R^3$ are as defined for Formula I, in the presence of a catalyst comprising palladium to form a compound of Formula I.

The present invention further pertains to aforesaid method wherein A is N-L in Formula I and further comprising before the hydrogenation step
(a) contacting a compound of Formula III,

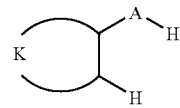

III wherein A is NH and K is as defined for Formula I, with a compound of Formula IV

IV $R^1R^2CHS(O)R^4$ wherein $R^4$ is $CHR^1R^2$ and $R^1$ and $R^2$ are as defined for Formula I, in the presence of an activating agent and adding a base at the same time or subsequently to the contact to form a compound of Formula V

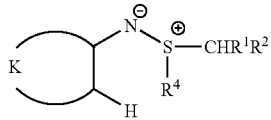

wherein K, $R^1$ and $R^2$ are defined for Formula I and $R^4$ is $CHR^1R^2$;

(b) rearranging the compound of Formula V to form a compound of Formula II wherein A is N-L, each L is H and n is 0;

(c) optionally acylating the compound of Formula II wherein each L is H to form a compound of Formula II wherein at least one L is an acyl group; and (d) optionally oxidizing the compound of Formula II wherein n is 0 to form a compound of Formula II wherein n is 1 or 2.

In particular, this invention pertains to a method for preparing a compound of Formula V

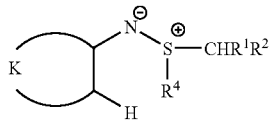

wherein

K is, together with the two contiguous linking carbon atoms, a phenyl ring, a 5- or 6-membered heteroaromatic ring or an aromatic 8-, 9- or 10-membered fused carbobicyclic or heterobicyclic ring system wherein each ring or ring system is optionally substituted;

$R^1$ is H, $C_1$ to $C_4$ alkyl or $CO_2R^3$;
$R^2$ is H or $C_1$ to $C_4$ alkyl;
$R^3$ is $C_1$ to $C_4$ alkyl; and
$R^4$ is $CHR^1R^2$;

the method comprising (a) contacting a compound of Formula III,

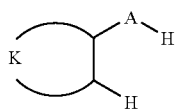

wherein A is NH and K is as defined for Formula V, with a compound of Formula IV $$R^1R^2CHS(O)R^4 \quad \text{IV}$$

wherein $R^4$ is $CHR^1R^2$ and $R^1$ and $R^2$ are as defined for Formula V, in an inert solvent and in the presence of sulfur trioxide as an activating agent to form a reaction product, and washing the reaction product in the inert solvent with an aqueous solution of a base to form the compound of Formula V.

This invention further relates to a method for preparing a compound of Formula II

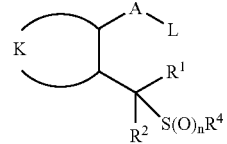

wherein
n is 0;
A is NH;
L is H;
K is, together with the two contiguous linking carbon atoms, a phenyl ring, a 5- or 6-membered heteroaromatic ring or an aromatic 8-, 9- or 10-membered fused carbobicyclic or heterobicyclic ring system wherein each ring or ring system is optionally substituted;
$R^1$ is H, $C_1$ to $C_4$ alkyl or $CO_2R^3$;
$R^2$ is H or $C_1$ to $C_4$ alkyl;
$R^3$ is $C_1$ to $C_4$ alkyl; and
$R^4$ is $CHR^1R^2$;

comprising the method described immediately above and a subsequent step of rearranging the compound of Formula V in a solvent to give the compound of Formula II.

This invention also pertains to novel compounds of Formulae I, II and V useful in these processes, such as S,S-dimethyl-N-[4-(trifluoromethyl)phenyl]sulfilimine, 2-[(methylthio)methyl]-4-(trifluoromethyl)benzenamine, and 2-[(methylsulfinyl)-methyl]-4-(trifluoromethyl)benzenamine.

DETAILED DESCRIPTION OF THE INVENTION

The term "alkyl", used either alone or in compound words such as "alkylaryl" includes straight-chain or branched alkyl, such as methyl, ethyl, propyl, i-propyl, or the different butyl, pentyl or hexyl isomers. "Alkoxy" includes, for example, methoxy, ethoxy, propyloxy, isopropyloxy and the different butoxy, pentoxy and hexyloxy isomers.

The term "halogen", either alone or in compound words such as "haloalkyl", includes fluorine, chlorine, bromine or iodine, with fluorine and chlorine preferred for the process of this invention.

As used herein, the term "aryl" refers to an aromatic ring system or a radical derived therefrom. The term "aromatic ring system" denotes fully unsaturated carbocycles and heterocycles in which the cyclic ring system is aromatic (where aromatic indicates that the Hückel rule is satisfied for the ring system). The term "aromatic carbobicyclic ring system" includes ring systems in which all ring members are carbon atoms and includes fully aromatic ring systems and ring systems in which at least one ring of a polycyclic ring system is aromatic (where aromatic indicates that the Hückel rule is satisfied). The term "heterocyclic ring" or "heterobicyclic ring system" denotes rings or ring systems in which at least one ring atom is not carbon and comprises 1 to 4 heteroatoms independently selected from the group consisting of nitrogen, oxygen and sulfur, provided that each heterocyclic ring contains no more than 4 nitrogens, no more than 2 oxygens and no more than 2 sulfurs. The heterocyclic ring can be attached through any available carbon or nitrogen by replacement of hydrogen on said carbon or nitrogen. The term "aromatic heterobicyclic ring system" includes fully aromatic heterocycles and heterocycles in which at least one ring of a polycyclic ring system is aromatic (where aromatic indicates that the Hückel rule is satisfied). Examples of suitable groups for K linked with the two contiguous carbon atoms are groups containing aromatic and heteroaromatic five and six-membered rings such as benzene, thiophene, pyridine, pyridazine, pyrazine, pyrimidine, triazine, triazole, pyrrole, imidazole, pyrazole, furan, oxazole, isoxazole, thiazole, thiadiazole, oxathiazole and polycyclic rings comprising combinations of the mononuclear aromatic structures, such as naphthalene, benzo[b] thiophene, benzofuran, quinoline, isoquinoline, quinoxaline, indole, isoindole, naphthyridine, indazole, benzopyrrole, benzotriazole, benzimidazole, benzoxazole, benzothiadiazole, and benzisothiazole. Additionally, bicyclic structures may be included, where one of the rings is aromatic and the other saturated. Examples include such compounds as 1,2, 3,4-tetrahydronapthalene, dihydroindole, dihydroisoindole and dihydrobenzopyran. An enormous variety of these aryl ring systems suitable for the process of the present invention, and methods for preparation of these aryl ring systems are well known in the art. For an extensive review see: *Comprehensive Organic Chemistry*, D. Barton and W. D. Ollis eds., Pergamon Press, NY, 1979, Volumes 1–6; *Comprehensive Heterocyclic Chemistry*, A. R. Katritzky and C. W. Rees eds., Pergamon Press, NY, 1984, Volumes 1–8; *Comprehensive Heterocyclic Chemistry II*, A. R. Katritzky, C. W. Rees and E. F. V. Scriven eds., Pergamon Press, NY, 1996, Volumes 1A–11; and the references cited therein.

Suitable substituents on the aryl group are those moieties that are not reducible under the palladium-catalyzed hydrogenation reaction conditions, which are understood by one skilled in the art. For a review of the susceptibility of organic groups to hydrogenation, see P. N. Rylander, *Catalytic Hydrogenation in Organic Syntheses*, Academic Press, NY, 1979 and M. Freifelder, *Catalytic Hydrogenation in Organic Synthesis Procedures and Commentary*, John Wiley & Sons, NY, 1978. For example, substituent groups resistant to these hydrogenation reaction conditions include such halogens as fluorine and chlorine; straight chain, branched and cycloalkyl groups; straight chain and branched alkoxy groups; straight chain and branched haloalkyl groups; straight chain and branched haloalkoxy groups; aryloxy groups (which can contain additional substituents such as alkyl) such as phenoxy; carboxylic acid groups; cyano groups; aryl and arylalkyl groups groups (which can contain additional substituents such as alkyl), for example, 4-methylbenzyl or 4-ethylpyridinyl.

Preferred are:
Preferred 1: Methods and compounds of this invention wherein A is other than O.
Preferred 2: Methods and compounds of this invention wherein $R^1$ is H or $CO_2CH_3$, $R^2$ is H and $R^4$ is $CH_3$ or $CH_2CO_2CH_3$.
Preferred 3: Methods and compounds of this invention wherein $R^1$ and $R^2$ are H.
Preferred 4: Methods and compounds of this invention wherein K, together with the two contiguous carbon atoms is optionally substituted with one or more groups independently selected from halogen, $C_1$–$C_4$ alkyl, $C_1$–$C_4$ alkoxy, $C_1$–$C_4$ haloalkyl and $C_1$–$C_4$ haloalkoxy.
Preferred 5: Methods and compounds of this invention wherein K, together with the two contiguous carbon atoms, is a phenyl ring optionally substituted with one or more groups independently selected from halogen, $C_1$–$C_4$ alkyl, $C_1$–$C_4$ alkoxy, $C_1$–$C_4$ haloalkyl, $C_1$–$C_4$ haloalkoxy, phenyl and phenoxy, each phenyl or phenoxy group optionally substituted with one or more groups independently selected from halogen, $C_1$–$C_4$ alkyl, $C_1$–$C_4$ alkoxy, $C_1$–$C_4$ haloalkyl and $C_1$–$C_4$ haloalkoxy.
Preferred 6: Methods and compounds of this invention wherein K, together with the two contiguous carbon atoms, is a phenyl ring optionally substituted with one or more groups independently selected from halogen, $C_1$–$C_4$ alkyl, $C_1$–$C_4$ alkoxy, $C_1$–$C_4$ haloalkyl and $C_1$–$C_4$ haloalkoxy.
Preferred 7: Methods and compounds of Preferred 6 wherein the phenyl ring is substituted with halogen, $C_1$–$C_4$ alkyl, $C_1$–$C_4$ alkoxy, $C_1$–$C_4$ haloalkyl or $C_1$–$C_4$ haloalkoxy para to A.

As shown in Scheme 1, ortho alkylated aromatic alcohols and amines, and their acylated derivatives, of Formula I can be prepared from compounds of Formula II.

Scheme I

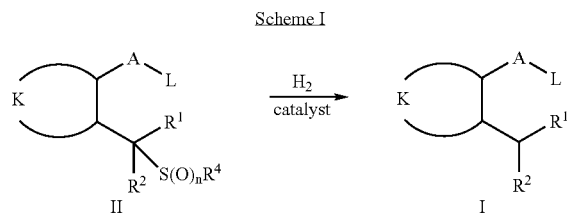

wherein
n is 0, 1 or 2;
A is O or N-L;
each L is independently H or an acyl group;
K is, together with the two contiguous linking carbon atoms, a phenyl ring, a 5- or 6-membered heteroaromatic ring or an aromatic 8-, 9- or 10-membered fused carbobicyclic or heterobicyclic ring system wherein each ring or ring system is optionally substituted;
$R^1$ is H, $C_1$ to $C_4$ alkyl or $CO_2R^3$;
$R^2$ is H or $C_1$ to $C_4$ alkyl;
$R^3$ is $C_1$ to $C_4$ alkyl; and
$R^4$ is $CHR^1R^2$.

In Formulae I and II, an acyl group as specified for L is understood to be a group linked by carbonyl, i.e. $C(O)$—$R^a$. $R^a$ can, in turn, be any group compatible with hydrogenation conditions, for example, H, $C_1$ to $C_4$ alkyl, $CF_3$, $C_1$ to $C_4$ alkoxy or $C_1$ to $C_4$ haloalkoxy. Each $R^a$ is selected independently for each occurrence of L.

The transformation shown in Scheme 1 can be achieved by the use of a catalyst comprising palladium in the presence of hydrogen. Preferably the catalyst comprises tin in addition to the palladium to resist poisoning by sulfur. The active portion of the catalyst can contain palladium and optionally tin alone, or it can further comprise other materials to enhance performance. A catalyst comprising tin from about 5% to about 20% of the weight of the palladium is preferred. (This means, for example, if 1000 mg of palladium is present then the amount of tin ranges from about 50 mg to about 200 mg.) More preferably, the tin content is from about 8% to about 12% of the weight of the palladium.

The catalyst employed in the present invention is preferably supported on a carrier, most preferably a carrier having a high specific surface area Such carriers include, for example, activated charcoal or carbon, silica gel, alumina or magnesia. Preferably the carrier is a porous particulate solid with a size distribution typically ranging from 5 to 100 μm for slurry applications and from about 0.8 to 4 mm for fixed bed applications and a BET (Brunauer-Emmett-Teller method) surface area typically ranging from about 300 to nearly 2000 m²/g. The catalyst carrier can be manufactured such as to have a latent acid, neutral or basic pH. Optionally the catalyst carrier can be treated prior to metal deposition by one or more techniques generally known in the art, such as impregnation with alkali metal salts and/or calcination or acid wash. Preferably the catalyst carrier is an activated charcoal or carbon support. Preferably the activated charcoal or carbon support has an average particle size on the order of 20 μm for slurry applications and 3 mm for fixed bed applications and a BET surface area from about 700 to about 1600 m²/g.

Palladium catalysts are typically prepared by contacting a palladium compound such as palladium(II) chloride with a reducing agent. By including a tin compound such as tin(II) chloride or tin(IV) chloride with the palladium compound, reduction provides a catalytic mixture of palladium and tin.

To prepare a palladium catalyst on a carrier, a standard method is to prepare a water solution of a soluble palladium compound such as palladium(II) chloride, preferably also containing hydrochloric acid, and add this solution to the carrier. The water is then evaporated to deposit the palladium compound in the carrier matrix. The solution can be added to the carrier by any technique generally known in the art, including by example but not limitation, immersion, spraying or the like. The dry or partially dry composite material is then contacted with a reducing agent for a period of time sufficient to reduce the palladium. Such procedures are described by R. Mozingo in *Organic Syntheses*, Collective Volume 3, Wiley, New York, 1955, pages 685–690.

To include tin in the palladium catalyst on a carrier, the above method can be modified to include a soluble tin compound, such as tin(II) chloride or tin(IV) chloride, in the solution of the soluble palladium compound before application to the carrier. Alternatively, separate solutions of the soluble palladium and soluble tin compounds can be prepared and sequentially applied to the carrier.

Optionally the catalyst precursor can be added to the hydrogenation reactor for the process of Scheme 1 wherein the reduction of palladium and tin occurs in situ in the hydrogenation reactor. Preferably the catalyst is prereduced with a reducing agent before use.

Alternative methods for preparing a palladium catalyst supported on a carrier include contacting with a reducing agent a mixture comprising suspended carrier and a solution of a soluble palladium optionally containing a soluble tin compound. Another method of preparing a supported palladium-tin catalyst involves evaporating a solution of a palladium compound onto the carrier and then applying vapor of a volatile tin compound, such as tin(IV) tetrachloride, to the carrier before contact with a reducing agent. Furthermore various other methods or alternate modes are possible for depositing the palladium and/or tin compounds on a carrier, such as by selective precipitation or the like, optionally with or without solvent washing such as to selectively remove less desired counterions.

As an alternative to applying the palladium and optional tin compounds to the carrier and then reducing, the carrier can be first impregnated with a reducing agent and then the palladium and optional tin compounds applied to the carrier. The residual reducing agent can then be washed or otherwise removed from the carrier. This method can preferentially deposit the metals near the surface of the carrier particles.

For preparing the catalyst, any palladium compound can be used that is water soluble. This includes by way of example, but not limitation, palladium(II) acetate, palladium (II) acetylacetonate, palladium(II) bromide and palladium (II) chloride. Palladium(II) chloride is generally preferred.

Tin compounds useful for preparing the catalyst include those that are water soluble or sufficiently volatile to enable vapor-phase deposition on a carrier. These include tin(II) chloride, tin(IV) chloride, tin(II) oxalate, tin(II) nitrate, sodium stannate and the like. Typically tin(II) chloride and tin(IV) chloride are used because of ready availability.

The reducing agent employed to chemically reduce the palladium and optionally tin can generally be any reductant or reducing environment consistent with either liquid phase reduction or vapor phase reduction, including by way of example, but not limitation, formaldehyde, sodium formate, glucose, acetaldehyde, sodium borohydride, hydrogen and the like. Reduction using hydrogen gas is a preferred method of reduction. Reduction using hydrogen gas can be conducted using a suspension of the solid catalyst precursor in a hydrogenation solvent such as ethyl acetate, tetrahydrofuran, toluene, acetic acid or acetic anhydride. When a solvent is employed using hydrogen gas, the temperature range is generally between ambient and 200° C. (preferably 50 to 150° C.), and the pressure is generally between atmospheric pressure and 20000 kPa. Preferably the reduction using hydrogen gas is conducted without solvent using a vapor phase comprising gaseous hydrogen with or without an inert gas such as nitrogen or the like in the presence of the solid catalyst precursor; generally such a vapor phase reduction is performed at a temperature range between ambient and 500° C. (preferably 100 to 300° C., most preferably 150 to 250° C.) at atmospheric pressure or up to a pressure of 20000 kPa.

Palladium catalysts including those containing tin are produced by Engelhard Corporation, Chemical Catalysts, Process Technologies Group, 101 Wood Avenue, Iselin, N.J. 08830-0770 U.S.A.

The reaction of Scheme 1 is usually conducted at pressures of $10^2$ to $10^4$ kPa (14.5 to 1450 psi) in a suitable organic solvent such as, but not limited to, ethyl acetate, tetrahydrofuran, toluene, acetic acid or acetic anhydride. Hydrogen pressures of around 1000 kPa generally achieve convenient rates of reaction. Elevated temperatures of 80 to 200° C. are usually required to achieve the transformation.

Shown in Scheme 1a is an illustrative subgenus of the transformation of Scheme 1 wherein K is, together with the two contiguous linking carbon atoms, an optionally substituted phenyl ring.

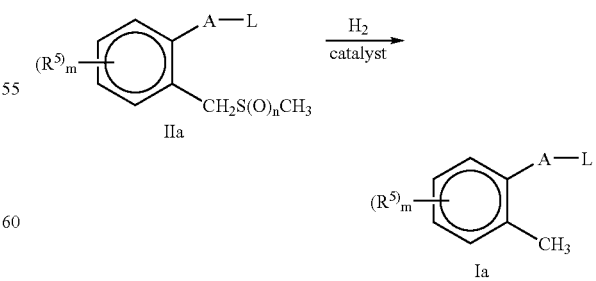

wherein n is 0, 1 or 2; A is O or N-L; each L is independently H or an acyl group C(O)—R$^a$; each R$^a$ is independently selected, for example, from H, $C_1$ to $C_4$ alkyl, $CF_3$, $C_1$ to $C_4$ alkoxy and $C_1$ to $C_4$ haloalkoxy; m is 0 to 4; and each $R^5$ is independently selected from halogen, $C_1$–$C_4$ alkyl, $C_1$–$C_4$ alkoxy, $C_1$–$C_4$ haloalkyl, $C_1$–$C_4$ haloalkoxy, phenyl or phenoxy, each phenyl or phenoxy group optionally substituted with groups independently selected from halogen, $C_1$–$C_4$ alkyl, $C_1$–$C_4$ alkoxy, $C_1$–$C_4$ haloalkyl and $C_1$–$C_4$ haloalkoxy.

As already mentioned, in the method of Schemes 1 and 1a, L can be H or an acyl group C(O)—$R^a$ wherein $R^a$ can be any group stable to hydrogenation such as H, $C_1$ to $C_4$ alkyl, $CF_3$, $C_1$ to $C_4$ alkoxy and $C_1$ to $C_4$ haloalkoxy. Because of the low cost of acetic anhydride, $R^a$ being methyl is preferred. As unacylated amino groups can potentially poison catalysts, acylating them can facilitate the method of Schemes 1 and 1a. Amino (i.e. A-L is $NH_2$) or hydroxy (i.e. A-L is OH) functions of Formulae II and IIa can be converted to acylated derivatives before contacting with hydrogen and catalyst, or as discussed below, acylation can be conducted in situ if the hydrogenation solvent comprises an acid anhydride.

A variety of methods for acylating amino and hydroxy functions are well known to those skilled in the art. Generally the process of acylating the A-L group of a compound of Formula II or IIa wherein A-L is OH or $NH_2$ involves contacting the compound with an acylating agent. Typical acylating agents are the corresponding acid halides, particularly chlorides (e.g., Cl—C(O)—$R^a$), and acid anhydrides (e.g., $R^a$—C(O)OC(O)—$R^a$). Acid anhydrides are more commonly used when $R^a$ is H or a carbon-linked group such as $C_1$ to $C_4$ alkyl and $CF_3$. When the desired acyl function is formyl (i.e., $R^a$ is H), the mixed anhydride H—C(O)OC(O)—$CH_3$ is particularly useful as the acylating agent. Acid halides are most useful as acylating agents when $R^a$ is other than H, for example, $C_1$ to $C_4$ alkyl, $CF_3$, $C_1$ to $C_4$ alkoxy and $C_1$ to $C_4$ haloalkoxy. Often the acylating reaction is conducted in a solvent inert to the acylating agent, such as dichloromethane, tetrahydrofuran or toluene. However, particularly with inexpensive acid anhydride acylating agents, such as acetic anhydride, it may be convenient to use the acylating agent as the solvent. As the acylating reaction generates an acid byproduct (carboxylic acids, e.g., HO—C(O)—$R^a$, from acid anhydride acylating agents, and hydrogen halides, e.g., HCl, from acid halide acylating agents), the reaction is often conducted in the presence of a base, particularly with acid halide acylating agents. Suitable bases can include tertiary amines such as triethylamine, diisopropylethylamine and the like, and inorganic bases such as alkali and alkaline earth metal carbonates. The acylation reaction can be performed in the presence of acylation catalysts, such as 4-(dimethylamino)pyridine. The acylation reaction is often conducted near ambient temperature, but can be conducted over a wide range of temperatures, such as between 0° C. and the boiling point of the solvent. The acylated product (i.e. Formula II or IIa wherein at least one L is an acyl group) can be isolated and purified by conventional means, such as evaporation of solvent, crystallization, chromatography, etc. For general procedures useful for acylating compounds of Formula II or IIa wherein A-L is OH or $NH_2$ see pp. 101–107 and pp. 223–266, respectively, of T. W. Greene, *Protective Groups in Organic Synthesis*, Wiley-Interscience, New York, 1981 and the references cited therein. This reference also describes methods of deacylating compounds to form free hydroxy and amino groups.

As already mentioned, even if each L in Formula II is H, the use of acetic or another acid anhydride as hydrogenation solvent can result in the acylated derivatives of Formula I. For example, in the reaction of Scheme 1a when each L in Formula IIa is H, use of acetic anhydride as solvent can produce acylated derivatives of Formula VIa when A is O and acylated derivatives of Formula VIb and diacylated aniline derivatives of Formula VIc when A is NH.

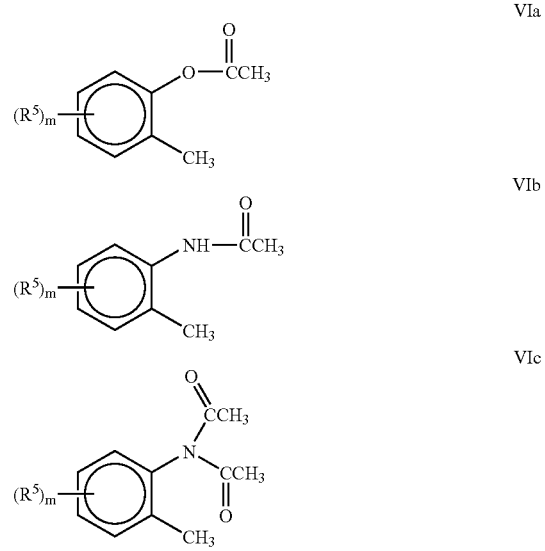

wherein m is 0 to 4; and each $R^5$ is independently selected from halogen, $C_1$–$C_4$ alkyl, $C_1$–$C_4$ alkoxy, $C_1$–$C_4$ haloalkyl, $C_1$–$C_4$ haloalkoxy, phenyl or phenoxy, each phenyl or phenoxy group optionally substituted with one or more groups independently selected from halogen, $C_1$–$C_4$ alkyl, $C_1$–$C_4$ alkoxy, $C_1$–$C_4$ haloalkyl and $C_1$–$C_4$ haloalkoxy.

The acetyl groups in Formulae VIa, VIb or VIc can be readily removed by standard chemical manipulations to provide compounds of Formula I. For example, removal of acetyl groups can be effected by treatment with hydrochloric acid in ethanol. With aromatic amines, e.g., Formulae VIb and VIc, this deacylation procedure will result in the formation of the hydrochloride salt of Formula Ia, which can be isolated or further processed with base to provide compounds of Formula Ia as the free bases. The conversion of compounds of Formulae VIa, VIb or VIc to compounds of Formula Ia may be accomplished either by isolating the compounds of Formulae VIa, VIb and VIc and removing the acetyl groups in a separate step or by treating the crude reaction products from the hydrogenation step directly.

In the method of Schemes 1 and 1a, n is typically 0, but as one skilled in the art will realize, numerous chemical modifications of the thioether moiety are possible and may be employed when necessary to facilitate this transformation. These include modifications wherein the thioether moiety is oxidized to the sulfoxide (n is 1) or sulfone (n is 2). Compounds of Formula II wherein n is 1 or 2 can be prepared by treating the corresponding compounds of Formula II wherein n is 0 with oxidizing agents, such as but not limited to, 3-chloroperoxybenzoic acid, in inert solvents, such as dichloromethane. A number of well-known procedures are available for the oxidation of sulfur; for example, see J. March, *Advanced Organic Chemistry;* 3rd edition, John Wiley: New York, (1985), p 1089. As this entails an additional reaction step, for the method of Schemes 1 and 1a, n is preferably 0.

As outlined in Scheme 2, compounds of Formula II wherein n is 0 can be prepared from the corresponding aromatic alcohols or amines of Formula I by treatment with the appropriate thioether of Formula VII and a chlorinating agent, such as tert-butyl hypochlorite or N-chlorosuccinimide, followed by treatment with a base, such as triethylamine or sodium methoxide in methanol, to effect rearrangement according to the methods described in P. G. Gassman, G. Gruetzmacher, *J. Am. Chem. Soc.* 1973, 95, 588–589, P. G. Gassman, G. Gruetzmacher, *Org. Syn.*, Coll. Vol. VI, 581–583; P. G. Gassman, H. R. Drewes, *J. Am. Chem. Soc.* 1978, 100, 7600–7610; and P. G. Gassman, D. R. Amick, *J. Am. Chem. Soc.* 1978, 100, 7611–7619.

Scheme 2

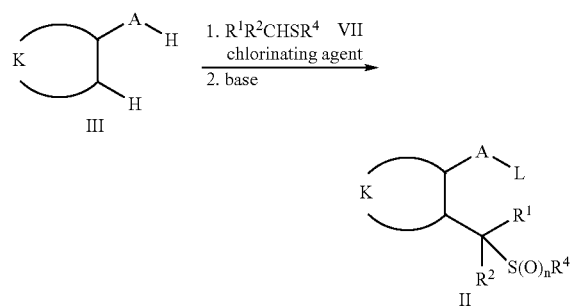

wherein
n is 0;
A is O or NH;
L is H;
K is, together with the two contiguous linking carbon atoms, a phenyl ring, a 5- or 6-membered heteroaromatic ring or an aromatic 8-, 9- or 10-membered fused carbobicyclic or heterobicyclic ring system wherein each ring or ring system is optionally substituted;
$R^1$ is H, $C_1$ to $C_4$ alkyl or $CO_2R^3$;
$R^2$ is H or $C_1$ to $C_4$ alkyl;
$R^3$ is $C_1$ to $C_4$ alkyl; and
$R^4$ is $CHR^1R^2$.

When A is NH, an intermediate ylid can be isolated after contacting the Formula III compound and thioether of Formula II with the chlorinating agent in a water-immiscible solvent and then washing with aqueous base such as sodium hydroxide solution; this ylid can then be rearranged to the compound of Formula II wherein n is 0 and L is H in the absence of solvent, in a protic solvent such as methanol or water, in an aprotic solvent in the presence of a suitable base, or in a combination of a protic solvent, an aprotic solvent and a base as described below for the conversion of Formula V to Formula II in Scheme 3.

Compounds of Formula II wherein n is 0, L is H and A is NH can also be prepared from the corresponding compounds of Formula III as shown in Scheme 3.

Scheme 3

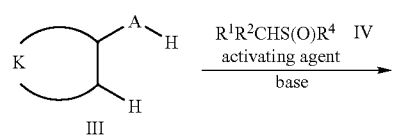

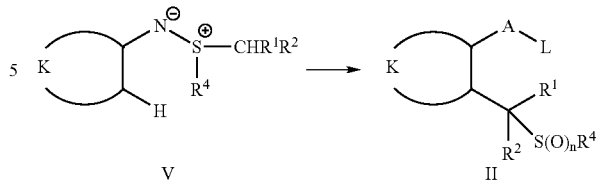

wherein
n is 0;
A is NH;
L is H;
K is, together with the two contiguous linking carbon atoms, a phenyl ring, a 5- or 6-membered heteroaromatic ring or an aromatic 8-, 9- or 10-membered fused carbobicyclic or heterobicyclic ring system wherein each ring or ring system is optionally substituted;
$R^1$ is H, $C_1$ to $C_4$ alkyl or $CO_2R^3$;
$R^2$ is H or $C_1$ to $C_4$ alkyl;
$R^3$ is $C_1$ to $C_4$ alkyl; and
$R^4$ is $CHR^1R^2$.

In the method of Scheme 3, intermediate sulfilimine (alternatively named iminosulfurane) ylid compounds of Formula V are prepared from aromatic amines of Formula III (A is NH) by reaction with a dialkyl sulfoxide of Formula IV which has been "activated" by treatment with an agent such as acetic anhydride, trifluoroacetic anhydride, trifluoromethanesulfonic anhydride, cyclohexylcarbodiimide, sulfur trioxide, or phosphorus pentoxide according to the procedures of P. Claus and W. Vycudilik *Tetrahedron Lett.* 1968, 3607–3610; *Monatsch. Chem.* 1970, 101, 396–404; and T. E. Varkey, G. F. Whitfield and D. Swern *J. Org. Chem.* 1974, 39, 3365–3372. The reaction is conducted in a suitable organic solvent such as dichloromethane or dimethyl sulfoxide. The reaction is conducted at a temperature between −70 and 25° C.; the optimal temperature depends on the solvent and reagent used.

In the method of Scheme 3, the intermediate ylid compounds of Formula V can be isolated or used without isolation in the subsequent rearrangement step. The rearrangement can be achieved in the absence of solvent (see U.S. Pat. No. 4,496,765), in a protic solvent such as methanol or water (see P. Claus and W. Rieder, *Monatsh. Chem.* 1972, 103, 1163–1177), in an aprotic solvent in the presence of a suitable base, or in a combination of a protic solvent, an aprotic solvent and a base. A variety of aprotic solvents can be used in this reaction, including chlorinated alkanes such as dichloromethane, ethers such as tetrahydrofuran, amides such as N,N-dimethyl-formamide, aromatic solvents such as benzene, chlorobenzene, toluene, xylene, etc. A variety of bases can be used, including tertiary alkyl and benzylamines like triethylamine, N,N-dimethylbenzylamine and 1,8-diazabicyclo[5.4.0]undec-7-ene, and alkali metal alkoxides such as sodium methoxide, sodium ethoxide and potassium tert-butoxide, which can be solubilized using crown ethers and the like. Alkali metal alkoxides are especially useful for effecting the rearrangement to Formula II in solvents comprising an aprotic solvent, and in particular, it has been discovered that a methanolic solution of sodium methoxide added to toluene as the bulk solvent works well for effecting the rearrangement. The temperature at which the reaction is conducted in solvents is usually in the range of about 40–110° C., but in the absence of solvent, the temperature needed is generally higher, i.e. about 100–200° C. When the reaction is conducted in the absence of solvent, inclusion of a catalytic amount of an organic base or weak acid such as succinimide as described by U.S. Pat. No. 4,496,765 can increase the rate of rearrangement. As one skilled in the art will realize, operable variations embraced by the method of Scheme 3 include generating a salt (e.g., a hydrochloride, sulfate or bisulfate) of the Formula V ylid, and then treating the salt with the appropriate amount of base to generate the free ylid of Formula V. This may be done as a separate step or an integral part of the step involving rearrangement to the compounds of Formula II.

Besides offering low cost and facilitating waste treatment, sulfur trioxide as activating agent in the method of Scheme 3 has been discovered to be effective in providing high yields of compounds of Formula II, which can then be reduced using the method of Scheme 1 to give compounds of Formula I. Accordingly this represents a preferred aspect of the present invention. Furthermore, the reaction using the sulfur trioxide complex of a sulfoxide compound of Formula IV has been discovered to be conveniently carried out with excellent yields using much smaller amounts of the Formula IV sulfoxide than directed by T. E. Varkey, G. F. Whitfield and D. Swern, *J. Org. Chem.* 1974, 39, 3365–3372 by conducting the reaction in an inert solvent. The solvent must be inert to the high electrophilicity of the complex of sulfur trioxide with the sulfoxide IV. Generally the solvent is chosen from fluorinated and chlorinated alkane and cycloalkane solvents. Specifically useful are solvents comprising at least one of dichloromethane and 1,1,2,2-tetrachloroethane. Most preferred for this reaction is a solvent comprising dichloromethane, which has been discovered to give excellent yields, as well as being relatively inexpensive and easily removed from the reaction product by evaporation. The reaction can generally be conducted in the range between the freezing and boiling point of the solvent, but is typically conducted between about −10 and 40° C.

Typically, nearly 2 moles of sulfur trioxide per mole of aromatic amine (Formula III, A is NH) has been found needed to obtain complete conversion, so the most useful amounts of sulfur trioxide are generally about 1.8 to 2.2 and more preferably about 1.9 to 2.1 equivalents relative to amount of the aromatic amine of Formula III. (As used herein one skilled in the art recognizes the term "equivalents" is effectively synonymous with the term "moles" for sulfur trioxide and the sulfoxide IV, and also for the aromatic amine III (A is NH) if it has a single amino functionality.) At least one mole of the sulfoxide IV per mole of aromatic amine is needed for complete conversion. Furthermore at least one mole of sulfoxide IV is typically used per mole of sulfur trioxide so that all of the sulfur trioxide is complexed. The solvent conditions of the present invention obviate need for considerable excesses of the sulfoxide IV, which would add to cost and waste treatment concerns. Therefore the amount of sulfoxide of Formula IV is generally in the range of about 0.5 to 3, more preferably in the range of about 1 to 2, and most preferably in the range of about 1 to 1.5 equivalents relative to the amount of sulfur trioxide. The amount of sulfoxide of Formula IV is generally in the range of about 1 to 6, more preferably in the range of about 1.8 to 4, and most preferably in the range of about 1.8 to 3 equivalents relative to the amount of aromatic amine of Formula III.

The reaction generally requires from 0.1 to 10 hours, and can be monitored by conventional techniques such as chromatography and nuclear magnetic resonance spectroscopy. After the reaction is complete, the reaction mixture is washed with an aqueous solution of base. The reaction between aromatic amine, sulfoxide and sulfur trioxide is believed to afford the product of Formula V in its protonated form. The base then liberates the free ylid species of Formula V as well as neutralizes other acidic byproducts in the reaction mixture. Accordingly, the amount of base is preferably at least 2 equivalents per each mole of sulfur trioxide used in the reaction, although typically an excess of base is used for convenience. Suitable bases include alkali metal carbonates, hydroxides and phosphates. For example, sodium hydroxide works well for this purpose. The ylid of Formula V can then be isolated by conventional techniques, such as evaporation of the solvent, crystallization, etc.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, T. W. Greene and P. G. M. Wuts, *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, "br s" means broad singlet.

EXAMPLE 1

Preparation of 2'-methyl-6'-phenoxyacetanilide

Step 1: Preparation of 2'-[(methylthio)methyl]-6'-phenoxyacetanilide

In a 3-necked, round bottom flask equipped with a mechanical stirrer 2-phenoxyaniline (37.0 g, 0.2 mol) was dissolved in dichloromethane (350 mL). A vigreux column was attached and part of the dichloromethane (100 mL) was distilled off. The reaction solution was then cooled to −5° C. using a dry ice/acetone bath. Dimethyl sulfide (18 mL, 0.25 mol) was added while the temperature of the reaction solution was maintained between −5 and 0° C. Then N-chlorosuccinimide (27.0 g, 0.2 mol) was added over a 10 minute period while the temperature of the reaction mixture was maintained between −5 and 0° C. After addition was complete, an ice/water bath was substituted for the dry ice/acetone bath to maintain the temperature near 0° C. while the reaction mixture was stirred for 30 minutes. Then triethylamine (60 mL, 0.42 mol) was added, and the mixture was heated at reflux for 2 hours. After the reaction mixture cooled to room temperature, a solution of sodium sulfite (20 g) in water (500 mL) was added to the stirred reaction mixture. After 10 minutes, the reaction mixture was decanted, and the organic layer was washed with water (500 mL). A 250 mL, 3-necked round bottom flask was fitted with a distillation head and an addition funnel. Part of the organic layer (100 mL) was poured into the flask, and the remainder of the organic layer was poured into the addition funnel. The organic layer material was added to the flask in 50 mL portions while solvent was removed by distillation. After all of the organic layer had been added and the flask temperature reached 110° C., the residual material was cooled to room temperature and diluted with cyclohexane (50 mL). The mixture was then heated to 60° C., and acetic anhydride (20 mL) was added over a 15 minute period. After the reaction mixture was held at 60° C. for one hour, it was cooled to room temperature and seeded with product crystals. After the mixture was stirred for one hour, the product was collected by filtration. The collected material was repeatedly washed with hexanes and petroleum ether and dried in vacuo to provide a crystalline product (24.41 g, 59% yield, 98% purity by gas chromatography area). This product was purified by recrystallization from toluene to afford product (13.24 g) that showed no impurity peaks by gas chromatography and $^1$H NMR.

Step 2: Preparation of 2'-methyl-6'-phenoxyacetanilide

Pressure tubes (C276 Hastalloy metal, 10 mL) were charged with 2'-[(methylthio)-methyl]-6'-phenoxyacetanilide (i.e. product of Step 1, weight listed in Table A for sulfide), catalyst (identity and weight listed in Table A) and solvent (identity and weight listed in Table A). With shaking, the contents of the pressure tubes were hydrogenated at the pressures, temperatures and periods of time listed in Table A. The catalysts were then removed by filtration, and the filtrates were analyzed by gas chromatography to determine percent conversion based on peak area.

TABLE A

Preparation of 2'-methyl-6'-phenoxyacetanilide by palladium-catalyzed hydrogenation of 2'-[(methylthio)methyl]-6'-phenoxyacetanilide

| Run | Catalyst* | Catalyst wt. (g) | Sulfide wt. (g) | Solvent | Solvent wt. (g) | Temp. (° C.) | Pressure (kPa) | Time (h) | % Conversion |
|---|---|---|---|---|---|---|---|---|---|
| 1 | Pd | 0.441 | 0.591 | EtOAc | 5.278 | 175 | 2760 | 4 | 98 |
| 2 | Pd | 0.385 | 0.518 | MeOH | 4.365 | 60 | 3450 | 4 | 10 |
| 3 | Pd | 0.445 | 0.600 | EtOAc | 5.288 | 175 | 1720 | 4 | 70 |
| 4 | Pd | 0.0438 | 0.594 | EtOAc | 5.288 | 175 | 2760 | 4 | 20 |
| 5 | Pd | 0.00934 | 0.583 | EtOAc | 5.273 | 175 | 2760 | 4 | 9 |
| 6 | Pd | 0.444 | 0.508 | EtOAc | 5.283 | 70 | 3450 | 4 | <5 |
| 7 | Pd | 0.443 | 0.500 | EtOAc | 5.279 | 70 | 3450 | 4 | <5 |
| 8 | Pd | 0.444 | 0.605 | Toluene | 5.270 | 175 | 2760 | 4 | 66 |
| 9 | Pd | 0.441 | 0.600 | EtOAc | 5.281 | 175 | 2760 | 4 | 95** |
| 10 | Pd-Sn | 0.045 | 0.594 | EtOAc | 5.278 | 175 | 2760 | 7 | 40 |
| 11 | None | — | 0.599 | EtOAc | 5.276 | 175 | 2760 | 4 | 12*** |

*Palladium (Pd) catalyst used was 5% palladium on carbon from Engelhard (864A-3-288-1). Palladium-tin (Pd-Sn) catalyst used was 5% palladium and 1% tin on carbon from Engelhard (864A-3-290-1).
**Unknown peak also seen by gas chromatography.
***Run 11 may suggest that the Hastalloy metal of the hydrogenation vessel has some catalytic properties.

EXAMPLE 2

Preparation of 2-methyl4-(trifluoromethyl)aniline as its Hydrochloride Salt

The gas chromatography (GC) analyses, for Example 2 used a Hewlett-Packard 5890 Series II Plus Gas Chromatograph with a 5 m long, 530 μm diameter HP-1 (dimethylpolysiloxane, available from Agilent Technologies) column and a thermal program of 90° C. for 1 min, then 20° C./min. increase to a final temperature of 250° C., which was held for 5 min. Helium was used as the carrier gas at a flow rate of 10 mL/min.

Step 1: Preparation of S,S-dimethyl-N-[4-(trifluoromethyl)phenyl]sulfilimine

Sulfur trioxide (4.84 g, 60.5 mmol) in dichloromethane (10 mL) was added to dimethyl sulfoxide (4.84 g, 62.0 mmol) in dichloromethane (10 mL) at −5 to 0° C. When the addition was complete 4-(trifluoromethyl)aniline (5.00 g, 31.0 mmol) was added dropwise. The mixture was allowed to warm to ambient temperature. After about 1 h the mixture was diluted with dichloromethane (80 mL) and washed with sodium hydroxide (1 N, 100 mL), dried and evaporated to give the title product as a solid (6.58 g, 96% yield).

$^1$H NMR (CDCl$_3$) δ 7.35 (d, 2H), 6.84 (d, 2H), 2.66 (s, 6H).

Step 2: Preparation of 2-[(methylthio)methyl]-4-(trifluoromethyl)benzenamine

Sodium methoxide in methanol (1.95 g, 25%, 9.02 mmol) was added to the product from Step 1 (2 g, 9.04 mmol) in toluene (15 mL). The mixture was warmed to about 80° C. After 1 h the mixture was allowed to cool and was poured into water (100 mL). The mixture was extracted with ethyl acetate (2×100 mL) and the combined extracts were dried and evaporated to give the title product as a solid (1.8 g, 90% yield), melting at 65.5–67.5° C. after recrystallization from hexanes.

IR (nujol) v 3419, 3333, 1629, 1584, 1512, 1440, 1334, 1302, 1235, 1194, 1139, 1078, 979, 904, 832 cm$^{-1}$. $^1$H NMR (CDCl$_3$) δ 7.35 (dd, J=8.2, 1.5 Hz, 1H), 7.26 (s, 1H), 6.72 (d, J=8.4 Hz, 1H), 4.39 (br s, 2H), 3.69 (s, 2H), 1.99 (3H, s). MS 221 (M$^+$).

Step 3: Preparation of N-[2-methyl-4-(trifluoromethyl)phenyl]acetamide

A glass-lined shaker tube was charged with the product from Step 2 (5.00 g, 22.6 mmol), catalyst (Engelhard 864A-3-290-1, 5% Pd, 1% Sn/C, 0.630 g), and acetic anhydride (80 mL). The tube was pressurized to 100 psi (690 kPa) with hydrogen at ambient temperature, then heated to 150° C. and shaken for 6 hours. The pressure was maintained at 140 psi (965 kPa) during this time by periodically repressurizing with hydrogen. After 6 hours, the reaction vessel was cooled to ambient temperature and the remaining hydrogen vented to release the pressure. GC analysis showed a mixture of the two products, N-[2-methyl-4-(trifluoromethyl)phenyl]acetamide and N-acetyl-N-[2-methyl-4-(trifluoromethyl)phenyl]acetamide, and the two acylated starting materials, N-[2-[(methylthio)methyl]-4-(trifluoromethyl)phenyl]acetamide and N-acetyl-N-[2-[(methylthio)methyl]-4-(trifluoromethyl)phenyl]acetamide, in a 6:55:6:33 peak area ratio, respectively.

The reaction mixture was filtered through Celite® diatomaceous filter aid, washed with ethyl acetate, and the filtrate concentrated in vacuo to an orange oil. To convert the N,N-diacetyl derivatives to their respective N-acetyl analogues, 4-(dimethyl-amino)pyridine (DMAP) (0.500 g) was added to a solution of the oil in ethanol (50 mL), and this solution was heated at reflux for 4 hours. GC analysis showed a 53:8:38:1 peak area ratio. After evaporation, the residue was purified by flash column chromatography (60:40 hexanes-ethyl acetate). N-[2-methyl-4-(trifluoromethyl)phenyl]acetamide was obtained as a white solid (2.85 g, 58% yield). The starting material was recovered as its acetylated derivative N-[2-[(methylthio)methyl]-4-(trifluoromethyl)phenyl]acetamide in 31% yield (1.84 g).

N-[2-methyl-4-(trifluoromethyl)phenyl]acetamide:

$^1$H NMR (CDCl$_3$) δ 8.074 (br d, 7.3 Hz, 1H), 7.4–7.5 (m, 2 H), 7.080 (br s, 1H), 2.313 (s, 3H), 2.235 (s, 3H). LC/MS AP$^+$: 218 (M$^+$+1) and 259 (M$^+$+1+41; acetonitrile adduct). m.p. 159.5–160.5° C. R$_f$ was 0.21 (60:40 hexanes-ethyl acetate), GC retention time: 3.52 min.

N-acetyl-N-[2-methyl4-(trifluoromethyl)phenyl]acetamide:

$^1$H NMR (CDCl$_3$) δ 7.599 (s, 1H), 7.570 (d, J=8.0 Hz, 1H), 7.214 (d, J=8.0 Hz, 1H), 2.278 (s, 6H), 2.230 (s, 3H). LC/MS AP$^+$: 259 (M$^+$–42+41; corresponding to acetonitrile adduct after loss of one acetyl group). m.p. 70–72° C. R$_f$ was 0.70 (60:40 hexanes-ethyl acetate). GC retention time: 3.432 min, peak was 97.8% of total area of all peaks recorded.

Step 4: Preparation of 2-methyl-4-(trifluoromethyl)aniline Hydrochloride

A solution of N-[2-methyl-4-(trifluoromethyl)phenyl]acetamide (5.17 g) and aqueous hydrochloric acid (37%, 12 mL) in ethanol (24 mL) was heated to reflux for 3 hours and then stirred at ambient temperature for 48 hours. GC analysis of the reaction mixture showed a 98:2 peak area ratio of 2-methyl-4-(trifluoromethyl)aniline to starting material. 2-Methyl-4-(trifluoromethyl)aniline hydrochloride was obtained as a white solid by filtering the reaction mixture and washing the solids with ethyl acetate. A second crop of 2-methyl-4-(trifluoromethyl)aniline hydrochloride was obtained by evaporating the filtrate to dryness, triturating the residue in ethyl acetate, then filtering, providing a total of 4.27 g (85% yield).

$^1$H NMR (CD$_3$OD) δ 7.726 (s, 1H), 7.664 (d, J=8.5 Hz, 1H), 7.544 (d, J=8.4 Hz, 1H), 2.484 (s, 3H). LC/MS AP$^+$: 176 (M$^+$), 217 (M$^+$+41, acetonitrile adduct). GC retention times: 1.74 min. for 2-methyl-4-(trifluoromethyl)aniline, 3.53 min. for N-[2-methyl-4-(trifluoromethyl)phenyl]acetamide.

By the methods described herein, including specifically the procedures illustrated by Example 1, together with methods known in the art, the following compounds of Tables 1A–3D can be prepared. The following abbreviations are used in the Tables which follow: t means tertiary, s means secondary, n means normal, i means iso, Me means methyl, Et means ethyl, Pr means propyl, i-Pr means isopropyl, Bu means butyl and Ph means phenyl. "Ex." refers to the above Examples.

TABLE 1A

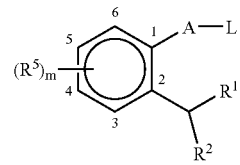

| R$^1$ | R$^2$ | (R$^5$)$_m$ | A | |
|---|---|---|---|---|
| | | L is H. | | |
| H | H | — | NH | |
| H | H | — | O | |
| Me | H | — | NH | |
| Me | H | — | O | |
| Me | Me | — | NH | |
| Me | Me | — | O | |
| Et | H | — | NH | |
| n-Bu | n-Bu | — | NH | |
| CO$_2$Me | H | — | NH | |
| CO$_2$Me | Me | — | NH | |
| CO$_2$Me | n-Bu | — | NH | |
| H | H | 4-F | NH | |
| H | H | 4-F | O | |
| H | H | 4-Cl | NH | |
| H | H | 4-Cl | O | |
| H | H | 4-Br | NH | |
| H | H | 4-Br | O | |
| H | H | 4-I | NH | |
| H | H | 4-I | O | |
| H | H | 4-CF$_3$ | NH | (Ex. 2, Step 4) |
| H | H | 4-CF$_3$ | O | |
| H | H | 4-Ph | NH | |
| H | H | 4-OPh | NH | |
| H | H | 6-OPh | NH | |
| H | H | 4-O(Ph-2'-Me) | NH | |
| H | H | 4-OCH$_3$ | NH | |
| H | H | 4-OCH$_3$ | O | |
| H | H | 4-OCF$_2$H | NH | |
| H | H | 4-OCF$_2$H | O | |
| H | H | 4-Me | NH | |
| H | H | 4-Me | O | |
| H | H | 4-OCH$_2$CF$_3$ | NH | |
| Me | H | 4-CF$_3$ | NH | |
| H | H | 3,5-di-Me | NH | |
| Me | Me | 4-CF$_3$ | NH | |
| Me | Me | 4-CF$_3$ | O | |
| Et | H | 4-CF$_3$ | NH | |
| n-Bu | n-Bu | 4-CF$_3$ | NH | |
| CO$_2$Me | H | 4-CF$_3$ | NH | |
| CO$_2$Me | Me | 4-CF$_3$ | NH | |
| CO$_2$Me | n-Bu | 4-CF$_3$ | NH | |
| H | H | 3,4,5-tri-Me | NH | |
| H | H | 3,4,5-tri-OMe | NH | |
| H | H | 6-CF$_3$ | NH | |
| H | H | 6-F | NH | |
| i-Pr | H | 4-CF$_3$ | NH | |
| H | H | 6-Ph | NH | |

TABLE 1A-continued

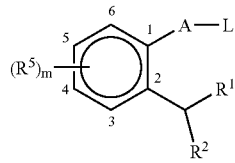

| $R^1$ | $R^2$ | $(R^5)_m$ | A |
|---|---|---|---|
| H | H | 6-Ph | O |
| H | H | 4-O(Ph-4'-Cl) | NH |
| H | H | 4-(Ph-4'-Cl) | NH |

L is C(O)CH₃.

| $R^1$ | $R^2$ | $(R^5)_m$ | A | |
|---|---|---|---|---|
| H | H | — | NH | |
| H | H | — | O | |
| Me | H | — | NH | |
| Me | H | — | O | |
| Me | Me | — | NH | |
| Me | Me | — | O | |
| Et | H | — | NH | |
| n-Bu | n-Bu | — | NH | |
| CO₂Me | H | — | NH | |
| CO₂Me | Me | — | NH | |
| CO₂Me | n-Bu | — | NH | |
| H | H | 4-F | NH | |
| H | H | 4-F | O | |
| H | H | 4-Cl | NH | |
| H | H | 4-Cl | O | |
| H | H | 4-Br | NH | |
| H | H | 4-Br | O | |
| H | H | 4-I | NH | |
| H | H | 4-I | O | |
| H | H | 4-CF₃ | NH | (Ex. 2, Step 3) |
| H | H | 4-CF₃ | O | |
| H | H | 4-Ph | NH | |
| H | H | 4-OPh | NH | |
| H | H | 6-OPh | NH | (Ex. 1, Step 2) |
| H | H | 4-O(Ph-2'-Me) | NH | |
| H | H | 4-OCH₃ | NH | |
| H | H | 4-OCH₃ | O | |
| H | H | 4-OCF₂H | NH | |
| H | H | 4-OCF₂H | O | |
| H | H | 4-Me | NH | |
| H | H | 4-Me | O | |
| H | H | 4-OCH₂CF₃ | NH | |
| Me | H | 4-CF₃ | NH | |
| H | H | 3,5-di-Me | NH | |
| Me | Me | 4-CF₃ | NH | |
| Me | Me | 4-CF₃ | O | |
| Et | H | 4-CF₃ | NH | |
| n-Bu | n-Bu | 4-CF₃ | NH | |
| CO₂Me | H | 4-CF₃ | NH | |
| CO₂Me | Me | 4-CF₃ | NH | |
| CO₂Me | n-Bu | 4-CF₃ | NH | |
| H | H | 3,4,5-tri-Me | NH | |
| H | H | 3,4,5-tri-OMe | NH | |
| H | H | 6-CF₃ | NH | |
| H | H | 6-F | NH | |
| i-Pr | H | 4-CF₃ | NH | |
| H | H | 6-Ph | NH | |
| H | H | 6-Ph | O | |
| H | H | 4-O(Ph-4'-Cl) | NH | |
| H | H | 4-(Ph-4'-Cl) | NH | |

| $R^1$ | $R^2$ | $(R^5)_m$ | A | L |
|---|---|---|---|---|
| H | H | — | NH | C(O)CH₂CH₃ |
| H | H | — | O | C(O)CH₂CH₃ |
| H | H | — | NH | C(O)CF₃ |
| H | H | — | NH | C(O)OCH₃ |
| H | H | — | O | C(O)OC(CH₃)₃ |
| H | H | — | NH | C(O)OC(CH₃)₃ |
| H | H | — | NH | C(O)OCH₂CH₂Cl |
| H | H | — | NH | C(O)O(CH₂)₃CH₃ |
| H | H | — | NH | C(O)(CH₂)₃CH₃ |

TABLE 1A-continued

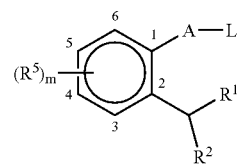

| $R^1$ | $R^2$ | $(R^5)_m$ | A | L |
|---|---|---|---|---|
| H | H | — | NH | C(O)H |
| Me | H | — | NH | C(O)CF₃ |
| Me | H | — | NH | C(O)OCH₃ |
| Me | Me | — | NH | C(O)OC(CH₃)₃ |
| H | H | 4-F | NH | C(O)O(CH₂)₂CH₃ |
| H | H | 4-Cl | O | C(O)CH₂CH₃ |
| H | H | 4-CF₃ | NH | C(O)OC(CH₃)₃ |
| H | H | 4-Me | NH | C(O)OCH₂CH₂Br |
| H | H | 6-CF₃ | NH | C(O)CF₃ |
| H | H | 6-F | NH | C(O)OCH₃ |
| H | H | 4-Ph | NH | C(O)OC(CH₃)₃ |
| H | H | 4-OPh | NH | C(O)(CH₂)₃CH₃ |
| H | H | 6-OPh | NH | C(O)CF₃ |
| H | H | 6-Ph | NH | C(O)OCH₂CH₃ |
| H | H | 4-OCH₃ | NH | C(O)CH₂CH₃ |
| H | H | 3,4,5-tri-Me | O | C(O)C(CH₃)₃ |
| H | H | 3,4,5-tri-OMe | NH | C(O)CF₃ |

TABLE 1B

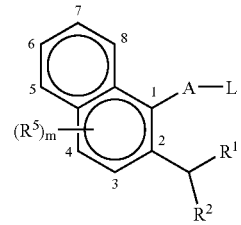

L is H.

| $R^1$ | $R^2$ | $(R^5)_m$ | A |
|---|---|---|---|
| H | H | — | NH |
| H | H | — | O |
| Me | H | — | NH |
| Me | H | — | O |
| Me | Me | — | NH |
| Et | H | — | NH |
| n-Bu | n-Bu | — | NH |
| CO₂Me | H | — | NH |
| CO₂Me | Me | — | NH |
| H | H | 4-F | NH |
| H | H | 4-F | O |
| H | H | 4-Cl | NH |
| H | H | 4-Br | NH |
| H | H | 4-CF₃ | NH |
| H | H | 4-OCH₃ | NH |
| H | H | 4-OCF₂H | NH |
| H | H | 4-Me | NH |
| H | H | 8-CH₃ | NH |
| Me | H | 4-CF₃ | NH |
| H | H | 3,5-di-Me | NH |
| Me | Me | 4-CF₃ | NH |
| Me | Me | 4-CF₃ | O |
| Et | H | 4-CF₃ | NH |
| n-Bu | n-Bu | 4-CF₃ | NH |
| CO₂Me | H | 4-CF₃ | NH |
| H | H | 6-CF₃ | NH |
| H | H | 6-F | NH |
| i-Pr | H | 4-CF₃ | NH |

TABLE 1B-continued

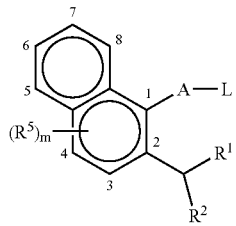

L is C(O)CH₃.

| R¹ | R² | (R⁵)ₘ | A |
|---|---|---|---|
| H | H | — | NH |
| H | H | — | O |
| Me | H | — | NH |
| Me | H | — | O |
| Me | Me | — | NH |
| Et | H | — | NH |
| n-Bu | n-Bu | — | NH |
| CO₂Me | H | — | NH |
| CO₂Me | Me | — | NH |
| H | H | 4-F | NH |
| H | H | 4-F | O |
| H | H | 4-Cl | NH |
| H | H | 4-Br | NH |
| H | H | 4-CF₃ | NH |
| H | H | 4-OCH₃ | NH |
| H | H | 4-OCF₂H | NH |
| H | H | 4-Me | NH |
| H | H | 8-CH₃ | NH |
| Me | H | 4-CF₃ | NH |
| H | H | 3,5-di-Me | NH |
| Me | Me | 4-CF₃ | NH |
| Me | Me | 4-CF₃ | O |
| Et | H | 4-CF₃ | NH |
| n-Bu | n-Bu | 4-CF₃ | NH |
| CO₂Me | H | 4-CF₃ | NH |
| H | H | 6-CF₃ | NH |
| H | H | 6-F | NH |
| i-Pr | H | 4-CF₃ | NH |

TABLE 1C

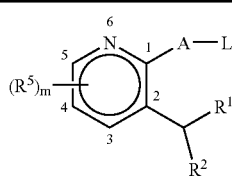

L is H.

| R¹ | R² | (R⁵)ₘ | A |
|---|---|---|---|
| H | H | — | NH |
| H | H | — | O |
| Me | H | — | NH |
| Me | H | — | O |
| Me | Me | — | NH |
| Et | H | — | NH |
| n-Bu | n-Bu | — | NH |
| CO₂Me | H | — | NH |
| CO₂Me | Me | — | NH |
| H | H | 4-F | NH |
| H | H | 4-F | O |
| H | H | 4-Cl | NH |
| H | H | 4-Br | NH |
| H | H | 4-CF₃ | NH |
| H | H | 4-OCH₃ | NH |
| H | H | 4-OCF₂H | NH |
| H | H | 4-Me | NH |

TABLE 1C-continued

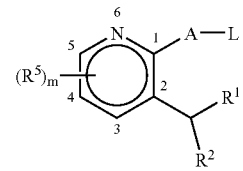

| H | H | 4-OCH₂CF₃ | NH |
|---|---|---|---|
| Me | H | 4-CF₃ | NH |
| H | H | 3,5-di-Me | NH |
| Me | Me | 4-CF₃ | NH |
| Me | Me | 4-CF₃ | O |
| Et | H | 4-CF₃ | NH |
| n-Bu | n-Bu | 4-CF₃ | NH |
| CO₂Me | H | 4-CF₃ | NH |
| i-Pr | H | 4-CF₃ | NH |

L is C(O)CH₃.

| R¹ | R² | (R⁵)ₘ | A |
|---|---|---|---|
| H | H | — | NH |
| H | H | — | O |
| Me | H | — | NH |
| Me | H | — | O |
| Me | Me | — | NH |
| Et | H | — | NH |
| n-Bu | n-Bu | — | NH |
| CO₂Me | H | — | NH |
| CO₂Me | Me | — | NH |
| H | H | 4-F | NH |
| H | H | 4-F | O |
| H | H | 4-Cl | NH |
| H | H | 4-Br | NH |
| H | H | 4-CF₃ | NH |
| H | H | 4-OCH₃ | NH |
| H | H | 4-OCF₂H | NH |
| H | H | 4-Me | NH |
| H | H | 4-OCH₂CF₃ | NH |
| Me | H | 4-CF₃ | NH |
| H | H | 3,5-di-Me | NH |
| Me | Me | 4-CF₃ | NH |
| Me | Me | 4-CF₃ | O |
| Et | H | 4-CF₃ | NH |
| n-Bu | n-Bu | 4-CF₃ | NH |
| CO₂Me | H | 4-CF₃ | NH |
| i-Pr | H | 4-CF₃ | NH |

TABLE 1D

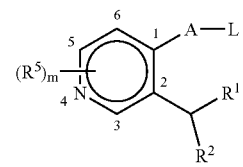

L is H.

| R¹ | R² | (R⁵)ₘ | A |
|---|---|---|---|
| H | H | — | NH |
| H | H | — | O |
| Me | H | — | NH |
| Me | H | — | O |
| Me | Me | — | NH |
| Et | H | — | NH |
| n-Bu | n-Bu | — | NH |
| CO₂Me | H | — | NH |
| CO₂Me | Me | — | NH |
| H | H | 6-F | NH |
| H | H | 6-F | O |
| H | H | 6-Cl | NH |

TABLE 1D-continued

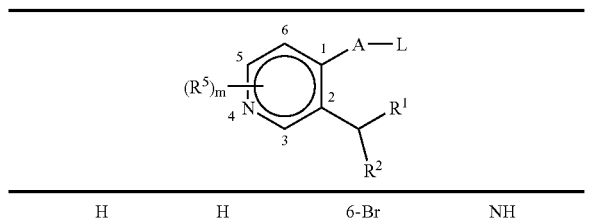

| R¹ | R² | (R⁵)ₘ | A |
|---|---|---|---|
| H | H | 6-Br | NH |
| H | H | 6-CF₃ | NH |
| H | H | 6-OCH₃ | NH |
| H | H | 6-OCF₂H | NH |
| H | H | 6-Me | NH |
| H | H | 6-OCH₂CF₃ | NH |
| Me | H | 6-CF₃ | NH |
| H | H | 3,5-di-Me | NH |
| Me | Me | 6-CF₃ | NH |
| Me | Me | 6-CF₃ | O |
| Et | H | 6-CF₃ | NH |
| n-Bu | n-Bu | 6-CF₃ | NH |
| CO₂Me | H | 6-CF₃ | NH |
| i-Pr | H | 6-CF₃ | NH |

L is C(O)CH₃.

| R¹ | R² | (R⁵)ₘ | A |
|---|---|---|---|
| H | H | — | NH |
| H | H | — | O |
| Me | H | — | NH |
| Me | H | — | O |
| Me | Me | — | NH |
| Et | H | — | NH |
| n-Bu | n-Bu | — | NH |
| CO₂Me | H | — | NH |
| CO₂Me | Me | — | NH |
| H | H | 6-F | NH |
| H | H | 6-F | O |
| H | H | 6-Cl | NH |
| H | H | 6-Br | NH |
| H | H | 6-CF₃ | NH |
| H | H | 6-OCH₃ | NH |
| H | H | 6-OCF₂H | NH |
| H | H | 6-Me | NH |
| H | H | 6-OCH₂CF₃ | NH |
| Me | H | 6-CF₃ | NH |
| H | H | 3,5-di-Me | NH |
| Me | Me | 6-CF₃ | NH |
| Me | Me | 6-CF₃ | O |
| Et | H | 6-CF₃ | NH |
| n-Bu | n-Bu | 6-CF₃ | NH |
| CO₂Me | H | 6-CF₃ | NH |
| i-Pr | H | 6-CF₃ | NH |

TABLE 2A

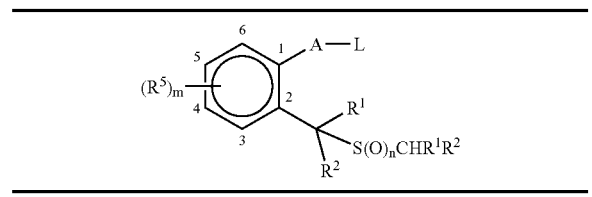

L is H, and n is 0.

| R¹ | R² | (R⁵)ₘ | A |
|---|---|---|---|
| H | H | — | NH |
| H | H | — | O |
| Me | H | — | NH |
| Me | H | — | O |
| Me | Me | — | NH |
| Me | Me | — | O |
| Et | H | — | NH |

TABLE 2A-continued

| R¹ | R² | (R⁵)ₘ | A | |
|---|---|---|---|---|
| n-Bu | n-Bu | — | NH | |
| CO₂Me | H | — | NH | |
| CO₂Me | Me | — | NH | |
| CO₂Me | n-Bu | — | NH | |
| H | H | 4-F | NH | |
| H | H | 4-F | O | |
| H | H | 4-Cl | NH | |
| H | H | 4-Cl | O | |
| H | H | 4-Br | NH | |
| H | H | 4-Br | O | |
| H | H | 4-I | NH | |
| H | H | 4-I | O | |
| H | H | 4-CF₃ | NH | (Ex. 2, Step 2) |
| H | H | 4-CF₃ | O | |
| H | H | 4-Ph | NH | |
| H | H | 4-OPh | NH | |
| H | H | 6-OPh | NH | |
| H | H | 4-O(Ph-2'-Me) | NH | |
| H | H | 4-OCH₃ | NH | |
| H | H | 4-OCH₃ | O | |
| H | H | 4-OCF₂H | NH | |
| H | H | 4-OCF₂H | O | |
| H | H | 4-Me | NH | |
| H | H | 4-Me | O | |
| H | H | 4-OCH₂CF₃ | NH | |
| Me | H | 4-CF₃ | NH | |
| H | H | 3,5-di-Me | NH | |
| Me | Me | 4-CF₃ | NH | |
| Me | Me | 4-CF₃ | O | |
| Et | H | 4-CF₃ | NH | |
| n-Bu | n-Bu | 4-CF₃ | NH | |
| CO₂Me | H | 4-CF₃ | NH | |
| CO₂Me | Me | 4-CF₃ | NH | |
| CO₂Me | n-Bu | 4-CF₃ | NH | |
| H | H | 3,4,5-tri-Me | NH | |
| H | H | 3,4,5-tri-OMe | NH | |
| H | H | 6-CF₃ | NH | |
| H | H | 6-F | NH | |
| i-Pr | H | 4-CF₃ | NH | |
| H | H | 6-Ph | NH | |
| H | H | 6-Ph | O | |
| H | H | 4-O(Ph-4'-Cl) | NH | |
| H | H | 4-(Ph-4'-Cl) | NH | |

L is C(O)CH₃, and n is 0.

| R¹ | R² | (R⁵)ₘ | A | |
|---|---|---|---|---|
| H | H | — | NH | |
| H | H | — | O | |
| Me | H | — | NH | |
| Me | H | — | O | |
| Me | Me | — | NH | |
| Me | Me | — | O | |
| Et | H | — | NH | |
| n-Bu | n-Bu | — | NH | |
| CO₂Me | H | — | NH | |
| CO₂Me | Me | — | NH | |
| CO₂Me | n-Bu | — | NH | |
| H | H | 4-F | NH | |
| H | H | 4-F | O | |
| H | H | 4-Cl | NH | |
| H | H | 4-Cl | O | |
| H | H | 4-Br | NH | |
| H | H | 4-Br | O | |
| H | H | 4-I | NH | |
| H | H | 4-I | O | |
| H | H | 4-CF₃ | NH | (Ex. 2, Step 2) |
| H | H | 4-CF₃ | O | |
| H | H | 4-Ph | NH | |

TABLE 2A-continued

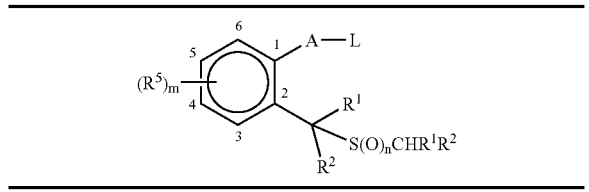

| R¹ | R² | (R⁵)ₘ | | |
|---|---|---|---|---|
| H | H | 4-OPh | NH | |
| H | H | 6-OPh | NH | (Ex. 1, Step 1) |
| H | H | 4-O(Ph-2'-Me) | NH | |
| H | H | 4-OCH₃ | NH | |
| H | H | 4-OCH₃ | O | |
| H | H | 4-OCF₂H | NH | |
| H | H | 4-OCF₂H | O | |
| H | H | 4-Me | NH | |
| H | H | 4-Me | O | |
| H | H | 4-OCH₂CF₃ | NH | |
| Me | H | 4-CF₃ | NH | |
| H | H | 3,5-di-Me | NH | |
| Me | Me | 4-CF₃ | NH | |
| Me | Me | 4-CF₃ | O | |
| Et | H | 4-CF₃ | NH | |
| n-Bu | n-Bu | 4-CF₃ | NH | |
| CO₂Me | H | 4-CF₃ | NH | |
| CO₂Me | Me | 4-CF₃ | NH | |
| CO₂Me | n-Bu | 4-CF₃ | NH | |
| H | H | 3,4,5-tri-Me | NH | |
| H | H | 3,4,5-tri-OMe | NH | |
| H | H | 6-CF₃ | NH | |
| H | H | 6-F | NH | |
| i-Pr | H | 4-CF₃ | NH | |
| H | H | 6-Ph | NH | |
| H | H | 6-Ph | O | |
| H | H | 4-O(Ph-4'-Cl) | NH | |
| H | H | 4-(Ph-4'-Cl) | NH | | n is 0.

| R¹ | R² | (R⁵)ₘ | A | L |
|---|---|---|---|---|
| H | H | — | NH | C(O)CH₂CH₃ |
| H | H | — | O | C(O)CH₂CH₃ |
| H | H | — | NH | C(O)CF₃ |
| H | H | — | NH | C(O)OCH₃ |
| H | H | — | O | C(O)OC(CH₃)₃ |
| H | H | — | NH | C(O)OC(CH₃)₃ |
| H | H | — | NH | C(O)OCH₂CH₂Cl |
| H | H | — | NH | C(O)O(CH₂)₃CH₃ |
| H | H | — | NH | C(O)(CH₂)₃CH₃ |
| H | H | — | NH | C(O)H |
| Me | H | — | NH | C(O)CF₃ |
| Me | H | — | NH | C(O)OCH₃ |
| Me | Me | — | NH | C(O)OC(CH₃)₃ |
| H | H | 4-F | NH | C(O)O(CH₂)₂CH₃ |
| H | H | 4-Cl | O | C(O)CH₂CH₃ |
| H | H | 4-CF₃ | NH | C(O)OC(CH₃)₃ |
| H | H | 4-Me | NH | C(O)OCH₂CH₂Br |
| H | H | 6-CF₃ | NH | C(O)CF₃ |
| H | H | 6-F | NH | C(O)OCH₃ |
| H | H | 4-Ph | NH | C(O)OC(CH₃)₃ |
| H | H | 4-OPh | NH | C(O)(CH₂)₃CH₃ |
| H | H | 6-OPh | NH | C(O)CF₃ |
| H | H | 6-Ph | NH | C(O)OCH₂CH₃ |
| H | H | 4-OCH₃ | NH | C(O)CH₂CH₃ |
| H | H | 3,4,5-tri-Me | O | C(O)C(CH₃)₃ |
| H | H | 3,4,5-tri-OMe | NH | C(O)CF₃ |

L is H, and n is 1.

| R¹ | R² | (R⁵)ₘ | A |
|---|---|---|---|
| H | H | — | NH |
| H | H | — | O |
| Me | H | — | NH |
| Me | H | — | O |
| Me | Me | — | NH |
| Me | Me | — | O |

TABLE 2A-continued

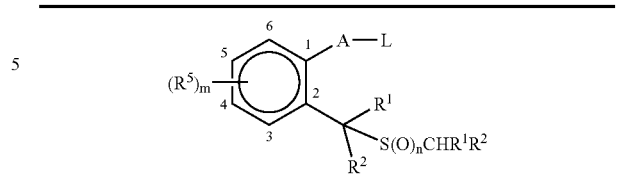

| R¹ | R² | (R⁵)ₘ | A |
|---|---|---|---|
| Et | H | — | NH |
| n-Bu | n-Bu | — | NH |
| CO₂Me | H | — | NH |
| CO₂Me | Me | — | NH |
| CO₂Me | n-Bu | — | NH |
| H | H | 4-F | NH |
| H | H | 4-F | O |
| H | H | 4-Cl | NH |
| H | H | 4-Cl | O |
| H | H | 4-Br | NH |
| H | H | 4-Br | O |
| H | H | 4-I | NH |
| H | H | 4-I | O |
| H | H | 4-CF₃ | NH |
| H | H | 4-CF₃ | O |
| H | H | 4-Ph | NH |
| H | H | 4-OPh | NH |
| H | H | 6-OPh | NH |
| H | H | 4-O(Ph-2'-Me) | NH |
| H | H | 4-OCH₃ | NH |
| H | H | 4-OCH₃ | O |
| H | H | 4-OCF₂H | NH |
| H | H | 4-OCF₂H | O |
| H | H | 4-Me | NH |
| H | H | 4-Me | O |
| H | H | 4-OCH₂CF₃ | NH |
| Me | H | 4-CF₃ | NH |
| H | H | 3,5-di-Me | NH |
| Me | Me | 4-CF₃ | NH |
| Me | Me | 4-CF₃ | O |
| Et | H | 4-CF₃ | NH |
| n-Bu | n-Bu | 4-CF₃ | NH |
| CO₂Me | H | 4-CF₃ | NH |
| CO₂Me | Me | 4-CF₃ | NH |
| CO₂Me | n-Bu | 4-CF₃ | NH |
| H | H | 3,4,5-tri-Me | NH |
| H | H | 3,4,5-tri-OMe | NH |
| H | H | 6-CF₃ | NH |
| H | H | 6-F | NH |
| i-Pr | H | 4-CF₃ | NH |
| H | H | 6-Ph | NH |
| H | H | 6-Ph | O |
| H | H | 4-O(Ph-4'-Cl) | NH |
| H | H | 4-(Ph-4'-Cl) | NH |

L is C(O)CH₃, and n is 1.

| R¹ | R² | (R⁵)ₘ | A |
|---|---|---|---|
| H | H | — | NH |
| H | H | — | O |
| Me | H | — | NH |
| Me | H | — | O |
| Me | Me | — | NH |
| Me | Me | — | O |
| Et | H | — | NH |
| n-Bu | n-Bu | — | NH |
| CO₂Me | H | — | NH |
| CO₂Me | Me | — | NH |
| CO₂Me | n-Bu | — | NH |
| H | H | 4-F | NH |
| H | H | 4-F | O |
| H | H | 4-Cl | NH |
| H | H | 4-Cl | O |
| H | H | 4-Br | NH |
| H | H | 4-Br | O |
| H | H | 4-I | NH |
| H | H | 4-I | O |
| H | H | 4-CF₃ | NH |
| H | H | 4-CF₃ | O |

TABLE 2A-continued

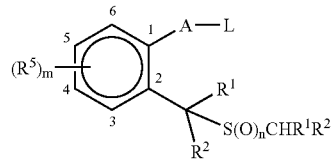

| R¹ | R² | (R⁵)ₘ | A |
|---|---|---|---|
| H | H | 4-Ph | NH |
| H | H | 4-OPh | NH |
| H | H | 6-OPh | NH |
| H | H | 4-O(Ph-2'-Me) | NH |
| H | H | 4-OCH₃ | NH |
| H | H | 4-OCH₃ | O |
| H | H | 4-OCF₂H | NH |
| H | H | 4-OCF₂H | O |
| H | H | 4-Me | NH |
| H | H | 4-Me | O |
| H | H | 4-OCH₂CF₃ | NH |
| Me | H | 4-CF₃ | NH |
| H | H | 3,5-di-Me | NH |
| Me | Me | 4-CF₃ | NH |
| Me | Me | 4-CF₃ | O |
| Et | H | 4-CF₃ | NH |
| n-Bu | n-Bu | 4-CF₃ | NH |
| CO₂Me | H | 4-CF₃ | NH |
| CO₂Me | Me | 4-CF₃ | NH |
| CO₂Me | n-Bu | 4-CF₃ | NH |
| H | H | 3,4,5-tri-Me | NH |
| H | H | 3,4,5-tri-OMe | NH |
| H | H | 6-CF₃ | NH |
| H | H | 6-F | NH |
| i-Pr | H | 4-CF₃ | NH |
| H | H | 6-Ph | NH |
| H | H | 6-Ph | O |
| H | H | 4-O(Ph-4'-Cl) | NH |
| H | H | 4-(Ph-4'-Cl) | NH |

L is H, and n is 2.

| R¹ | R² | (R⁵)ₘ | A |
|---|---|---|---|
| H | H | — | NH |
| H | H | — | O |
| Me | H | — | NH |
| Me | H | — | O |
| Me | Me | — | NH |
| Me | Me | — | O |
| Et | H | — | NH |
| n-Bu | n-Bu | — | NH |
| CO₂Me | H | — | NH |
| CO₂Me | Me | — | NH |
| CO₂Me | n-Bu | — | NH |
| H | H | 4-F | NH |
| H | H | 4-F | O |
| H | H | 4-Cl | NH |
| H | H | 4-Cl | O |
| H | H | 4-Br | NH |
| H | H | 4-Br | O |
| H | H | 4-I | NH |
| H | H | 4-I | O |
| H | H | 4-CF₃ | NH |
| H | H | 4-CF₃ | O |
| H | H | 4-Ph | NH |
| H | H | 4-OPh | NH |
| H | H | 6-OPh | NH |
| H | H | 4-O(Ph-2'-Me) | NH |
| H | H | 4-OCH₃ | NH |
| H | H | 4-OCH₃ | O |
| H | H | 4-OCF₂H | NH |
| H | H | 4-OCF₂H | O |
| H | H | 4-Me | NH |
| H | H | 4-Me | O |
| H | H | 4-OCH₂CF₃ | NH |
| Me | H | 4-CF₃ | NH |
| H | H | 3,5-di-Me | NH |
| Me | Me | 4-CF₃ | NH |
| Me | Me | 4-CF₃ | O |

TABLE 2A-continued

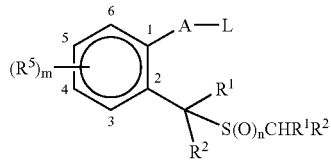

| R¹ | R² | (R⁵)ₘ | A |
|---|---|---|---|
| Et | H | 4-CF₃ | NH |
| n-Bu | n-Bu | 4-CF₃ | NH |
| CO₂Me | H | 4-CF₃ | NH |
| CO₂Me | Me | 4-CF₃ | NH |
| CO₂Me | n-Bu | 4-CF₃ | NH |
| H | H | 3,4,5-tri-Me | NH |
| H | H | 3,4,5-tri-OMe | NH |
| H | H | 6-CF₃ | NH |
| H | H | 6-F | NH |
| i-Pr | H | 4-CF₃ | NH |
| H | H | 6-Ph | NH |
| H | H | 6-Ph | O |
| H | H | 4-O(Ph-4'-Cl) | NH |
| H | H | 4-(Ph-4'-Cl) | NH |

L is C(O)CH₃, and n is 2.

| R¹ | R² | (R⁵)ₘ | A |
|---|---|---|---|
| H | H | — | NH |
| H | H | — | O |
| Me | H | — | NH |
| Me | H | — | O |
| Me | Me | — | NH |
| Me | Me | — | O |
| Et | H | — | NH |
| n-Bu | n-Bu | — | NH |
| CO₂Me | H | — | NH |
| CO₂Me | Me | — | NH |
| CO₂Me | n-Bu | — | NH |
| H | H | 4-F | NH |
| H | H | 4-F | O |
| H | H | 4-Cl | NH |
| H | H | 4-Cl | O |
| H | H | 4-Br | NH |
| H | H | 4-Br | O |
| H | H | 4-I | NH |
| H | H | 4-I | O |
| H | H | 4-CF₃ | NH |
| H | H | 4-CF₃ | O |
| H | H | 4-Ph | NH |
| H | H | 4-OPh | NH |
| H | H | 6-OPh | NH |
| H | H | 4-O(Ph-2'-Me) | NH |
| H | H | 4-OCH₃ | NH |
| H | H | 4-OCH₃ | O |
| H | H | 4-OCF₂H | NH |
| H | H | 4-OCF₂H | O |
| H | H | 4-Me | NH |
| H | H | 4-Me | O |
| H | H | 4-OCH₂CF₃ | NH |
| Me | H | 4-CF₃ | NH |
| H | H | 3,5-di-Me | NH |
| Me | Me | 4-CF₃ | NH |
| Me | Me | 4-CF₃ | O |
| Et | H | 4-CF₃ | NH |
| n-Bu | n-Bu | 4-CF₃ | NH |
| CO₂Me | H | 4-CF₃ | NH |
| CO₂Me | Me | 4-CF₃ | NH |
| CO₂Me | n-Bu | 4-CF₃ | NH |
| H | H | 3,4,5-tri-Me | NH |
| H | H | 3,4,5-tri-OMe | NH |
| H | H | 6-CF₃ | NH |
| H | H | 6-F | NH |
| i-Pr | H | 4-CF₃ | NH |
| H | H | 6-Ph | NH |
| H | H | 6-Ph | O |
| H | H | 4-O(Ph-4'-Cl) | NH |
| H | H | 4-(Ph-4'-Cl) | NH |

TABLE 2B

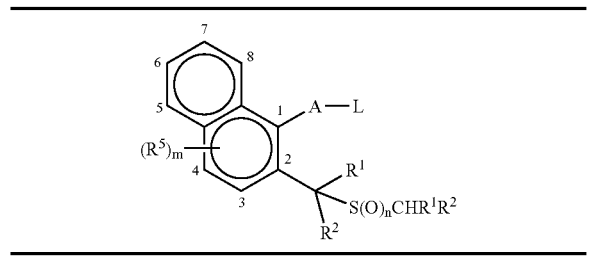

| R¹ | R² | (R⁵)ₘ | A |
|---|---|---|---|
| \multicolumn{4}{c}{L is H, and n is 0.} | | | |
| H | H | — | NH |
| H | H | — | O |
| Me | H | — | NH |
| Me | H | — | O |
| Me | Me | — | NH |
| Et | H | — | NH |
| n-Bu | n-Bu | — | NH |
| CO₂Me | H | — | NH |
| CO₂Me | Me | — | NH |
| H | H | 4-F | NH |
| H | H | 4-F | O |
| H | H | 4-Cl | NH |
| H | H | 4-Br | NH |
| H | H | 4-CF₃ | NH |
| H | H | 4-OCH₃ | NH |
| H | H | 4-OCF₂H | NH |
| H | H | 4-Me | NH |
| H | H | 8-CH₃ | NH |
| Me | H | 4-CF₃ | NH |
| H | H | 3,5-di-Me | NH |
| Me | Me | 4-CF₃ | NH |
| Me | Me | 4-CF₃ | O |
| Et | H | 4-CF₃ | NH |
| n-Bu | n-Bu | 4-CF₃ | NH |
| CO₂Me | H | 4-CF₃ | NH |
| H | H | 6-CF₃ | NH |
| H | H | 6-F | NH |
| i-Pr | H | 4-CF₃ | NH |

| R¹ | R² | (R⁵)ₘ | A |
|---|---|---|---|
| \multicolumn{4}{c}{L is C(O)CH₃, and n is 0.} | | | |
| H | H | — | NH |
| H | H | — | O |
| Me | H | — | NH |
| Me | H | — | O |
| Me | Me | — | NH |
| Et | H | — | NH |
| n-Bu | n-Bu | — | NH |
| CO₂Me | H | — | NH |
| CO₂Me | Me | — | NH |
| H | H | 4-F | NH |
| H | H | 4-F | O |
| H | H | 4-Cl | NH |
| H | H | 4-Br | NH |
| H | H | 4-CF₃ | NH |
| H | H | 4-OCH₃ | NH |
| H | H | 4-OCF₂H | NH |
| H | H | 4-Me | NH |
| H | H | 8-CH₃ | NH |
| Me | H | 4-CF₃ | NH |
| H | H | 3,5-di-Me | NH |
| Me | Me | 4-CF₃ | NH |
| Me | Me | 4-CF₃ | O |
| Et | H | 4-CF₃ | NH |
| n-Bu | n-Bu | 4-CF₃ | NH |
| CO₂Me | H | 4-CF₃ | NH |
| H | H | 6-CF₃ | NH |
| H | H | 6-F | NH |
| i-Pr | H | 4-CF₃ | NH |

TABLE 2C

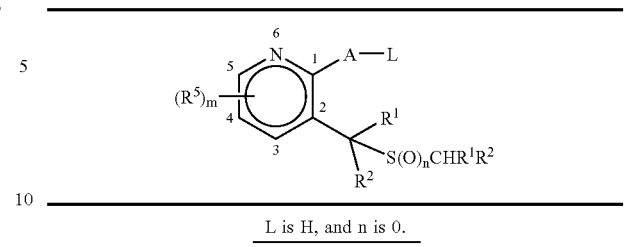

| R¹ | R² | (R⁵)ₘ | A |
|---|---|---|---|
| \multicolumn{4}{c}{L is H, and n is 0.} | | | |
| H | H | — | NH |
| H | H | — | O |
| Me | H | — | NH |
| Me | H | — | O |
| Me | Me | — | NH |
| Et | H | — | NH |
| n-Bu | n-Bu | — | NH |
| CO₂Me | H | — | NH |
| CO₂Me | Me | — | NH |
| H | H | 4-F | NH |
| H | H | 4-F | O |
| H | H | 4-Cl | NH |
| H | H | 4-Br | NH |
| H | H | 4-CF₃ | NH |
| H | H | 4-OCH₃ | NH |
| H | H | 4-OCF₂H | NH |
| H | H | 4-Me | NH |
| H | H | 4-OCH₂CF₃ | NH |
| Me | H | 4-CF₃ | NH |
| H | H | 3,5-di-Me | NH |
| Me | Me | 4-CF₃ | NH |
| Me | Me | 4-CF₃ | O |
| Et | H | 4-CF₃ | NH |
| n-Bu | n-Bu | 4-CF₃ | NH |
| CO₂Me | H | 4-CF₃ | NH |
| i-Pr | H | 4-CF₃ | NH |

| R¹ | R² | (R⁵)ₘ | A |
|---|---|---|---|
| \multicolumn{4}{c}{L is C(O)CH₃, and n is 0.} | | | |
| H | H | — | NH |
| H | H | — | O |
| Me | H | — | NH |
| Me | H | — | O |
| Me | Me | — | NH |
| Et | H | — | NH |
| n-Bu | n-Bu | — | NH |
| CO₂Me | H | — | NH |
| CO₂Me | Me | — | NH |
| H | H | 4-F | NH |
| H | H | 4-F | O |
| H | H | 4-Cl | NH |
| H | H | 4-Br | NH |
| H | H | 4-CF₃ | NH |
| H | H | 4-OCH₃ | NH |
| H | H | 4-OCF₂H | NH |
| H | H | 4-Me | NH |
| H | H | 4-OCH₂CF₃ | NH |
| Me | H | 4-CF₃ | NH |
| H | H | 3,5-di-Me | NH |
| Me | Me | 4-CF₃ | NH |
| Me | Me | 4-CF₃ | O |
| Et | H | 4-CF₃ | NH |
| n-Bu | n-Bu | 4-CF₃ | NH |
| CO₂Me | H | 4-CF₃ | NH |
| i-Pr | H | 4-CF₃ | NH |

TABLE 2D

L is H, and n is 0.

| R¹ | R² | (R⁵)$_m$ | A |
|---|---|---|---|
| H | H | — | NH |
| H | H | — | O |
| Me | H | — | NH |
| Me | H | — | O |
| Me | Me | — | NH |
| Et | H | — | NH |
| n-Bu | n-Bu | — | NH |
| CO₂Me | H | — | NH |
| CO₂Me | Me | — | NH |
| H | H | 6-F | NH |
| H | H | 6-F | O |
| H | H | 6-Cl | NH |
| H | H | 6-Br | NH |
| H | H | 6-CF₃ | NH |
| H | H | 6-OCH₃ | NH |
| H | H | 6-OCF₂H | NH |
| H | H | 6-Me | NH |
| H | H | 6-OCH₂CF₃ | NH |
| Me | H | 6-CF₃ | NH |
| H | H | 3,5-di-Me | NH |
| Me | Me | 6-CF₃ | NH |
| Me | Me | 6-CF₃ | O |
| Et | H | 6-CF₃ | NH |
| n-Bu | n-Bu | 6-CF₃ | NH |
| CO₂Me | H | 6-CF₃ | NH |
| i-Pr | H | 6-CF₃ | NH |

L is C(O)CH₃, and n is 0.

| R¹ | R² | (R⁵)$_m$ | A |
|---|---|---|---|
| H | H | — | NH |
| H | H | — | O |
| Me | H | — | NH |
| Me | H | — | O |
| Me | Me | — | NH |
| Et | H | — | NH |
| n-Bu | n-Bu | — | NH |
| CO₂Me | H | — | NH |
| CO₂Me | Me | — | NH |
| H | H | 6-F | NH |
| H | H | 6-F | O |
| H | H | 6-Cl | NH |
| H | H | 6-Br | NH |
| H | H | 6-CF₃ | NH |
| H | H | 6-OCH₃ | NH |
| H | H | 6-OCF₂H | NH |
| H | H | 6-Me | NH |
| H | H | 6-OCH₂CF₃ | NH |
| Me | H | 6-CF₃ | NH |
| H | H | 3,5-di-Me | NH |
| Me | Me | 6-CF₃ | NH |
| Me | Me | 6-CF₃ | O |
| Et | H | 6-CF₃ | NH |
| n-Bu | n-Bu | 6-CF₃ | NH |
| CO₂Me | H | 6-CF₃ | NH |
| i-Pr | H | 6-CF₃ | NH |

TABLE 3A

| R¹ | R² | (R⁵)$_m$ | |
|---|---|---|---|
| H | H | — | |
| Me | H | — | |
| Me | Me | — | |
| Et | H | — | |
| n-Bu | n-Bu | — | |
| CO₂Me | H | — | |
| CO₂Me | Me | — | |
| CO₂Me | n-Bu | — | |
| H | H | 4-F | |
| H | H | 4-Cl | |
| H | H | 4-Br | |
| H | H | 4-I | |
| H | H | 4-CF₃ | (Ex. 2, Step 1) |
| H | H | 4-OCH₃ | |
| H | H | 4-OCF₂H | |
| H | H | 4-Ph | |
| H | H | 6-OPh | |
| H | H | 4-O(Ph-2'-Me) | |
| H | H | 4-Me | |
| H | H | 4-OCH₂CF₃ | |
| Me | H | 4-CF₃ | |
| H | H | 3,5-di-Me | |
| Me | Me | 4-CF₃ | |
| Et | H | 4-CF₃ | |
| n-Bu | n-Bu | 4-CF₃ | |
| CO₂Me | H | 4-CF₃ | |
| CO₂Me | Me | 4-CF₃ | |
| CO₂Me | n-Bu | 4-CF₃ | |
| H | H | 3,4,5-tri-Me | |
| H | H | 3,4,5-tri-OMe | |
| H | H | 6-CF₃ | |
| H | H | 6-F | |
| i-Pr | H | 4-CF₃ | |
| H | H | 6-Ph | |
| H | H | 4-O(Ph-4'-Cl) | |
| H | H | 4-(Ph-4'-Cl) | |

TABLE 3B

| R¹ | R² | (R⁵)$_m$ |
|---|---|---|
| H | H | — |
| Me | H | — |
| Me | Me | — |
| Et | H | — |
| n-Bu | n-Bu | — |
| CO₂Me | H | — |
| CO₂Me | Me | — |
| H | H | 4-F |
| H | H | 4-Cl |
| H | H | 4-Br |
| H | H | 4-CF₃ |
| H | H | 4-OCH₃ |
| H | H | 4-OCF₂H |
| H | H | 4-Me |
| H | H | 8-CH₃ |

TABLE 3B-continued

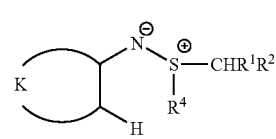

| R¹ | R² | (R⁵)ₘ |
|---|---|---|
| Me | H | 4-CF₃ |
| H | H | 3,5-di-Me |
| Me | Me | 4-CF₃ |
| Et | H | 4-CF₃ |
| n-Bu | n-Bu | 4-CF₃ |
| CO₂Me | H | 4-CF₃ |
| H | H | 6-CF₃ |
| H | H | 6-F |
| i-Pr | H | 4-CF₃ |

TABLE 3C

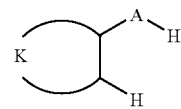

| R¹ | R² | (R⁵)ₘ |
|---|---|---|
| H | H | — |
| Me | H | — |
| Me | Me | — |
| Et | H | — |
| n-Bu | n-Bu | — |
| CO₂Me | H | — |
| CO₂Me | Me | — |
| H | H | 4-F |
| H | H | 4-Cl |
| H | H | 4-Br |
| H | H | 4-CF₃ |
| H | H | 4-OCH₃ |
| H | H | 4-OCF₂H |
| H | H | 4-Me |
| H | H | 4-OCH₂CF₃ |
| Me | H | 4-CF₃ |
| H | H | 3,5-di-Me |
| Me | Me | 4-CF₃ |
| Et | H | 4-CF₃ |
| n-Bu | n-Bu | 4-CF₃ |
| CO₂Me | H | 4-CF₃ |
| i-Pr | H | 4-CF₃ |

TABLE 3D

| R¹ | R² | (R⁵)ₘ |
|---|---|---|
| H | H | — |
| Me | H | — |
| Me | Me | — |
| Et | H | — |
| n-Bu | n-Bu | — |
| CO₂Me | H | — |

TABLE 3D-continued

| R¹ | R² | (R⁵)ₘ |
|---|---|---|
| CO₂Me | Me | — |
| H | H | 6-F |
| H | H | 6-Cl |
| H | H | 6-Br |
| H | H | 6-CF₃ |
| H | H | 6-OCH₃ |
| H | H | 6-OCF₂H |
| H | H | 6-Me |
| H | H | 6-OCH₂CF₃ |
| Me | H | 6-CF₃ |
| H | H | 3,5-di-Me |
| Me | Me | 6-CF₃ |
| Et | H | 6-CF₃ |
| n-Bu | n-Bu | 6-CF₃ |
| CO₂Me | H | 6-CF₃ |
| i-Pr | H | 6-CF₃ |

What is claimed is:

1. A method for preparing a compound of Formula V $$\underset{K}{\diagdown}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\! \overset{N^{\ominus}}{\underset{H}{\overset{|}{C}}}\!\!-\!\!\overset{\oplus}{\underset{R^{4}}{S}}\!\!-\!\!CHR^{1}R^{2} \qquad V$$

wherein
  K is, together with the two contiguous linking carbon atoms, a phenyl ring, a 5- or 6-membered heteroaromatic ring or an aromatic 8-, 9- or 10-membered fused carbobicyclic or heterobicyclic ring system wherein each ring or ring system is optionally substituted;
  R¹ is H, C₁ to C₄ alkyl or CO₂R³;
  R² is H or C₁ to C₄ alkyl;
  R³ is C₁ to C₄ alkyl; and
  R⁴ is CHR¹R²;
the method comprising
  contacting a compound of Formula III, $$\underset{K}{\diagdown}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\! \overset{A\diagdown H}{\underset{H}{\overset{|}{C}}} \qquad III$$

wherein A is NH and K is as defined for Formula V, with a compound of Formula IV

R¹R²CHS(O)R⁴    IV wherein R⁴ is CHR¹R² and R¹ and R² are as defined for Formula V, in dichloromethane as an inert solvent and in the presence of sulfur trioxide as an activating agent to form a reaction product, and washing the reaction product in the inert solvent with an aqueous solution of a base to form the compound of Formula V.

2. The method of claim 1 wherein the base is selected from an alkali metal carbonate, hydroxide or phosphate.

3. The method of claim 1 wherein the amount of sulfur trioxide is about 1.8 to 2.2 equivalents relative to the amount of the compound of Formula III.

4. The method of claim 3 wherein the amount of sulfur trioxide is about 1.9 to 2.1 equivalents relative to the amount of the compound of Formula III.

5. The method of claim 1 wherein the amount of the compound of Formula IV is about 0.5 to 3 equivalents relative to the amount of sulfur trioxide.

6. The method of claim 5 wherein the amount of the compound of Formula IV is about 1 to 2 equivalents relative to the amount of sulfur trioxide.

7. The method of any of claims 1 through 6 wherein $R^1$ is H or $CO_2CH_3$, $R^2$ is H, and $R^4$ is $CH_3$ or $CH_2CO_2CH_3$.

8. The method of claim 7 wherein $R^1$ is H, $R^2$ is H and $R^4$ is $CH_3$.

9. The method of any of claims 1 through 6 wherein K, together with the two contiguous carbon atoms, is a phenyl ring optionally substituted with one or more groups independently selected from halogen, $C_1$–$C_4$ alkyl, $C_1$–$C_4$ alkoxy, $C_1$–$C_4$ haloalkyl, $C_1$–$C_4$ haloalkoxy, phenyl and phenoxy, each phenyl or phenoxy group optionally substituted with one or more groups independently selected from halogen, $C_1$–$C_4$ alkyl, $C_1$–$C_4$ alkoxy, $C_1$–$C_4$ haloalkyl and $C_1$–$C_4$ haloalkoxy.

* * * * *